(12) United States Patent
Gearheart et al.

(10) Patent No.: US 6,423,533 B1
(45) Date of Patent: Jul. 23, 2002

(54) ISOLATION AND USE OF PERCHLORATE AND NITRATE REDUCING BACTERIA

(76) Inventors: Robert A. Gearheart, 613 Park Ave., Arcata, CA (US) 95521; Michael Ives, 650 Holmes La., McKinleyville, CA (US) 95519

( * ) Notice: Subject to any disclaimer, the term of this patent is extended or adjusted under 35 U.S.C. 154(b) by 0 days.

(21) Appl. No.: 09/713,902

(22) Filed: Nov. 16, 2000

Related U.S. Application Data

(60) Provisional application No. 60/165,691, filed on Nov. 16, 1999.

(51) Int. Cl.$^7$ .............................. C12N 1/20; C12S 13/00
(52) U.S. Cl. .............................. 435/262.5; 435/252.11; 210/610; 210/611
(58) Field of Search .............................. 435/262, 262.5, 435/254, 252.1, 822, 831; 210/610, 611

(56) References Cited

U.S. PATENT DOCUMENTS

| | | | |
|---|---|---|---|
| 3,755,156 A | | 8/1973 | Yakovlev et al. |
| 3,943,055 A | | 3/1976 | Korenkov et al. |
| 4,853,334 A | * | 8/1989 | Vandenbergh et al. |
| 5,302,285 A | | 4/1994 | Attaway et al. |
| 5,891,339 A | | 4/1999 | Van Ginkel et al. |
| 5,948,260 A | | 9/1999 | Attaway, III et al. |
| 6,066,257 A | | 5/2000 | Venkatesh et al. |
| 6,077,429 A | | 6/2000 | Frankenberger, Jr. et al. |
| 6,077,432 A | | 6/2000 | Coppola et al. |

OTHER PUBLICATIONS

Anbar, M., S. Guttmann and Z. Lewitus. 1959. The mode of action of perchlorate ions on the iodine uptake of the thyroid gland. Int. J. Appl. Radiat. Isot. 7:87–96.

Attaway, H. and M. Smith. 1993. Reduction of perchlorate by an anaerobic enrichment culture. J. Industrial Microbiology 12:408–412.

Coates, J.D., U. Michaelidou, R.A. Bruce, S.M. O'Connor, J.N. Crespi and L.A. Achenbach. 1999. Ubiquity and diversity of dissimilatory (per)chlorate–reducing bacteria. Appl. Environ. Microbiol. 65(12):5234–5241.

Dendooven, L. and J.M. Anderson. 1994. Dynamics of reduction enzymes involved in the denitrification process in pasture soil. Soil Biol. Biochem. 26 (11):1501–1506.

Dendooven, L. and J.M. Anderson. 1995. Use of a ileast squarei optimization procedure to estimate enzyme characteristics and substrate affinities in the denitrification reactions in soil.Soil Biol. Biochem 27 (10):1261–1270.

Focht, D.D. 1994. Microbiological procedures for biodegradation research. p 407–426. In "Methods of Soil Analysis", Part 2. SSSA Book Ser. 5. SSSA, Madison, WI.

Giblin, T.L., D.C. Herman and W.T. Frankenberger, Jr. 1999. An autotrophic system for the bioremediation of perchlorate from groundwater, p. 199–211, in "Perchlorate in the Environment" (E.T. Urbansky, ed). Kluwer Academic/Plenum Publishers, New York, NY.

Giblin, T., D. Herman, M.A. Deshusses and W.T. Frankenberger, Jr. 2000. Removal of perchlorate in groundwater with a flow–through bioreactor. J. Environ. Qual. 29:578–583.

Herman, D.C. and W.T. Frankenberger Jr. 1999. Bioremediation and biodegradation, bacterial reduction of perchlorate and nitrate in water. J. Environ. Qual. 28:1018–1024.

Logan, B.E., K. Kim, J. Miller, P. Mulvaney, J. Wu, H. Zhang and R. Unz. 1999. Factors affecting biodegradation of perchlorate contaminated waters. In "Proceedings of the Perchlorate in the Environment Symposium", Aug. 22–26, 1999 (E.T. Urbansky and M.R. Schock, eds). Division of Environmental Chemistry, American Chemical Society, New Orleans, LA.

Malmqvist. A., T. Welander, and L. Gunnarsson. 1991. Anaerobic growth of microorganisms with chlorate as an electron acceptor. Appl. Environ. Microbiol. 57(8):2229–2232.

Malmqvist, A., T. Welander, E. Moore, A. Ternstrom, G. Molin, ad I.M. Stenstrom. 1994. Ideonella dechloratans gen. nov., sp. nov., a new bacterium capable of growing anaerobically with chlorate as an electron acceptor. System. Appl. Microbiol. 17:58–64.

Michaelidou, U., L.A. Achenbach and J.D. Coates. 1999. Isolation and characterization of two novel (per)chlorate–reducing bacteria from swine waste lagoons In "Proceedings of the Perchlorate in the Environment Symposium", Aug. 22–26, 1999 (E.T. Urbansky and M.R. Schock., eds). Division of Environmental Chemistry, American Chemical Society, New Orleans. LA.

Miller, J.P. and B.E. Logan. 2000. Sustained perchlorate degradation in an autotrophic, gas–phase, packed–bed bioreactor. Environ. Sci. Technol. 34:3018–3022.

(List continued on next page.)

*Primary Examiner*—William H. Beisner
(74) *Attorney, Agent, or Firm*—Gallagher & Kennedy, P.A.; Thomas D. MacBlain

(57) ABSTRACT

Methods and compositions for removing perchlorate and/or nitrate from contaminated material utilizing a DM-17 bacteria. DM-17 is a gram-negative, motile, polymorphic, facultative anaerobe which is deposited with the American Type Culture Collection under ATCC No. PTA-2685. DM-17 may be used as a substitute for anaerobic bacteria which are presently being used in biological systems for removing perchlorate and/or nitrate from water and other contaminated materials, such as soil. Enhancement of nitrate reduction results from the presence of a level of perchlorate. Enhancement of perchlorate results from the presence of a level of nitrate. Particular carbon contributors further enhance remediation.

44 Claims, 11 Drawing Sheets

OTHER PUBLICATIONS

Nzengung, V.A. and C. Wang. 1999. Influences on phytoremediation of perchlorate contaminated water. In "Proceedings of the Perchlorate in the Environment Symposium", Aug. 22–26, 1999 (E.T. Urbansky and M.R. Schock, eds). Division of Environmental Chemistry, American Chemical Society, New Orleans, LA.

Rikken, G.B., A.G.M. Kroon and C.G. van Ginkel. 1996. Transformation of (per)chlorate into chloride by a newly isolated bacterium; reduction and dismutation. Appl. Microbiol. Biotechnol. 45:420–426.

Sokal R.R. and F.J. Rohlf. 1981. Biometry: The Principles and practice of statistics in biological research. W.H. Freeman, San Francisco, California.

Wallace, W.T., T. Ward, A. Breen, and H. Attaway. 1996. Identification of an anaerobic bacterium which reduces perchlorate and chlorate as Wolinella succinogenes. J. Ind. Microbiol. 16:68–72.

Wolff, J. 1998. Perchlorate and the thyroid gland. Pharmacol. Rev. 50:89–105.

Bergy's Manual. 1984. Bergy's Manual of Systematic Bacteriology, Edited by N.R.Krieg. Williams and Wilkins, Baltimore, Maryland.

Stanbury, J.B. and J.B. Wyngaardin. 1952. Effect of perchlorate on the human thyroid gland. Metabolism 1:533–539.

* cited by examiner

ISOLATION AND USE OF PERCHLORATE AND NITRATE REDUCING BACTERIA

CROSS REFERENCE TO RELATED APPLICATION

Priority is claimed from U.S. Provisional Application Serial No. 60/165,691, filed Nov. 16, 1999 for all subject matter common hereto. That provisional application is incorporated by reference herein.

FIELD OF INVENTION

This invention relates to perchlorate and nitrate metabolizing bacteria, their isolation and method of use. More particularly, this invention relates to bacteria useful in the remediation of perchlorate and nitrate contaminated materials and means and materials to enhance such remediation.

BACKGROUND

The use of bacteria to treat perchlorate and nitrate contaminated material such as soil and water is described in the "Description of Related Art" of U.S. Pat. No. 6,077,429 of William T. Frankenberger, Jr. and David Herman, issued Jun. 20, 2000, entitled *Bacterial Removal of Perchlorate and Nitrate,* which patent is incorporated herein by reference. As discussed by Coates, Michaelidou, Bruce, O'Connor, Crespi, and Achenbach, in *Ubiquity and Diversity of Dissimilatory (Per)chlorate-Reducing Bacteria,* in *Applied and Environmental Microbiology,* December, 1999, only six organisms capable of obtaining energy for growth by the metabolism of compounds containing oxyanions of chlorine, such as perchlorates, had previously been identified at the time of Coates et al. writing, even though the use of such microbes to reduce such compounds has been known for more than fifty years. The Coates et al. article is incorporated herein by reference.

Coates et al. point out that the discovery of a phylogenitically diverse group of organisms that had evolved with the ability to couple growth to the reduction of perchlorate was unexpected. Also unexpected was the discovery of perchlorate metabolizing bacteria in environments free of perchlorates. Frankenberger et al. teach that the presence of nitrate inhibits the reduction of perchlorate by a perchlorate metabolizing bacterium.

Perchlorate is a strong oxidizing agent in its associated form and is principally manufactured as the oxidizing component in propellants and explosives. In its aqueous ionic form, the perchlorate oxyanion is extremely stable and mobile, making effective treatment difficult and expensive. It has been estimated that under typical ground and surface water conditions, the perchlorate anion may persist for decades. As the concern of perchlorate in groundwater has taken on new importance nationwide, multiple studies are currently being conducted that focus on improved analytical methods, human health assessments, ecological impact assessments, and improved treatment technologies.

It has long been known that perchlorate has the potential to perturbate the mammalian hypothalamic-pituitary-thyroid axis. Specifically, perchlorate inhibits thyroid iodide anion uptake through the action of competitive binding. This leads to reduced T3 and T4 thyroid hormones, resulting in excess Thyroid Stimulating Hormone (TSH) by the pituitary gland (Anbar et al., 1959; Stanbury and Wyngaarden, 1952; Wolff, J., 1998). Prolonged perturbations may ultimately result in thyroid neoplasia, especially in sensitive rodent species. The California Department of Health Services has adopted an action level of 18 $\mu$g $L^{-1}$ perchlorate in drinking water.

A 4.4 acre constructed wetland system, at the Apache Powder Superfund Site (APS) in Cochise County, Arizona, referred to as the Northern Area Remediation System (NARS), consisting of three primary denitrification cells, an aerobic nitrification cell, and a final denitrification cell, is intended to denitrify high levels of nitrate found in the shallow aquifer. Previous engineering design and modeling efforts for NARS did not anticipate the presence of perchlorate. Therefore, after perchlorate discovery at APS in 1998, the inventors established the current study to investigate the possibility that perchlorate would interfere with or diminish the capability of the NARS to treat nitrate containing groundwater.

Data regarding the effects of perchlorate on denitrification is generally limited. Herman and Frankenberger, Jr. (1999), using a bacterial isolate known as perclace, found a decrease in the rate of denitrification when the concentrations of nitrate and perchlorate were equal at 1 mM, requiring 48 h for complete reduction. However, when perchlorate levels were reduced to 0.089 mg $L^{-1}$, complete nitrate reduction required only 24 h. However, Herman and Frankenberger, Jr. (1999) focused on a single bacterial isolate and not on the assemblage of microorganisms known to denitrify. One aspect of the current study focused on determining the potential effects of high levels of perchlorate on a mixed inoculant sampled from an operating wetland wastewater treatment system.

Dendooven and Anderson (1994) reported that in the presence of perchlorate, nitrous oxide production was low during the first 3–4 h, then increased sharply at 4 h and held constant for the next 20 h. After 24 h, all of the nitrate was reduced and very little nitrous oxide was produced. They suggest the lag time was due to two factors, the persistence of oxygen which delayed the de-repression of the reduction enzyme system and the kinetics of the denitrification process.

Strategies for the removal of perchlorate based on adsorption by activated carbon or use of reverse osmosis and ion exchange have not shown remediation solutions as promising as biological processes. Microorganisms utilization to degrade perchlorate in anaerobic or microaerophylic conditions to innocuous end-product, namely chloride are by far the most promising perchlorate remediation technology. Such biological treatment can be further used for the simultaneous treatment of perchlorate and nitrate. Wetlands typically contain extensive anaerobic or microaerophylic environments due to natural decomposition of plants, algae, fungi, bacteria and other organic material. Therefore, the current study also initiated preliminary treatability experiments designed to determine if enriched or non-enriched wetland derived cultures are capable of perchlorate reduction and to determine baseline kinetics.

Identified perchlorate reducers fall into several different categories. Coates et al. (1999) investigated six different environments including pristine soil, paper mill waste sludge, heavy metal contaminated aquatic sediments, hydrocarbon contaminated lake sediments, hydrocarbon contaminated soils, and animal waste treatment sludge. They recovered perchlorate reducers from all six environments. Coates et al. (1999) isolated 13 (per)chlorate reducing bacteria (CIRB), eight of which were characterized. Collectively, they represent broad phylogenetic diversities. All of the isolates were members of Proteobacteria. These bacteria were typified as being motile, gram-negative, non-fermentative, and facultative anaerobes. Their optimum growth occurred at 35° C., pH 7.5 and 1% NaCl. All could utilize acetate, propionate, isobutyrate, butyrate, valerate, malate, fumerate and lactate as electron donors, while none could utilize methanol, catechol, glycerol, citrate, glucose or hydrogen. All of the characterized bacteria could use chlorate and oxygen as electron acceptors, but could not utilize sulfate, selenate, fumerate, malate, Mn(IV), or Fe(III). Coates et al. (1999) suggests these genera may be the dominant perchlorate reducing bacteria in the environment. Coates et al. (1999) identified and named two species of perchlorate reducers in the β sub-division of Proteobacteria, *Dechlorimonas agitatus* and *Dechlorosoma suilla*.

In a related study, Michaelidou et al. (1999) isolated two Proteobacteria strains from a swine waste lagoon. They were both typified by being non-fermentative, mesophilic, motile, gram-negative bacteria. One strain, designated as PS, was rod-shaped and 0.2 μm by 2 μm in length and placed within the β sub-division of Proteobacteria. Nearly complete 16S rRNA sequencing indicated that the closest known relative was *Rhodocyclus tenuis*. The second strain, designated as WD, was placed into the α sub-division and shared 94.6% similarity to *Magnetospirillum gryphiswaldense*. Strain WD grew as a spirillum, but did not produce magnetosomes when grown in iron based media and there was no indication of magnetotaxis. Malmqvist et al. (1991) also discusses an enriched culture containing helical bacteria capable of reducing chlorate to chloride. Malmqvist et al. (1994) later describes the novel bacteria as *Ideonella dechloratans*, however, *I. dechloratans* and DM-17 share only 89% 16S rRNA gene homology.

A number of other perchlorate reducing bacteria have been studied. Rikken et al. (1996) isolated a bacteria (GR-1) from activated sludge. Sequencing of the 16S rRNA did not yield a match, but placed GR-1 in the β sub-division of Proteobacteria. The bacteria could use perchlorate, chlorate, oxygen, nitrate and Mn(IV) as electron acceptors. They also found that the GR-1 utilizes acetate, proprionate, caprionate, malate, succinate and lactate, but could not catabolize citrate, glycine, glycolate or formate. The inventors have also found that their isolate, DM-17, could not catabolize citrate. Rikken et al. (1996) also state that GR-1 was capable of completely reducing 800 mg $L^{-1}$ of perchlorate in 9 d. The inventors found that DM-17 in static culture could completely reduce 1000 mg $L^{-1}$ of perchlorate in 7 d.

Using a nutrient broth-yeast extract culture medium, Attaway and Smith (1993) enriched a perchlorate reducing mixed culture (gram positive cocci/rods and gram negative rods) isolated from anaerobic digester sludge. They found that the culture could use perchlorate, chlorate, chlorite, nitrate, nitrite and sulfate as electron acceptors. In contrast, Rikken et al. (1996) pointed out that GR-1 could not grow solely on chlorite because the dismutation reaction yields no energy to be used for biosynthesis. Attaway and Smith (1993) also discuss a reproducible lag time of 15–24 h prior to perchlorate reduction. The inventors' study also showed a regular lag time of 48–72 h. However, the inventors believe the discrepancy was related to differences in initial biomass and culture medium. They found that high biomass cultures introduced into fresh media containing 10 mM perchlorate resulted in rapid and instantaneous reduction of perchlorate.

Attaway and Smith (1993) indicated that the bacteria comprising the mixed culture were strict anaerobes and that any introduction of oxygen slowed or eliminated perchlorate reduction. In fact, perchlorate reduction could only be measured when the resazurin indicator turned colorless (Eh below −110 mV) and once the resazurin turned pink, all perchlorate reduction ceased. Attaway and Smith (1993) suggest that transient chloride oxides such as chlorite and hypochlorite may be responsible for the oxidation of the resazurin indicator in oxygen free media. In contrast, the present study by the inventors showed that DM-17 effectively reduced perchlorate when the resazurin indicator was pink (Eh above −110 mV) indicating a slightly oxidized environment. Another explanation suggested by Rikken et al. (1996), is that dismutation of chlorite by GR-1 generates oxygen. Since the dismutation is the final step in converting perchlorate to chloride, it is possible that the pink color of the inventors' cultures resulted from the dismutation of chlorite. This explanation is favored because the inventors' cultures became colorless once perchlorate could no longer be detected by probe (<10 μM). This is important because the bacteria studied by Attaway and Smith (1993) were strict anaerobes and the culture medium had to maintain strictly anaerobic conditions by addition of reducing agents such as cysteine hydrochloride. In the case of bacterial isolates DM-17 and GR-1, no media manipulation was required.

Attaway and Smith (1993) also state that their cultures permanently lost the ability to reduce perchlorate when exposed to oxygen for 12 to 24 h. The DM-17 and GR-1 isolates were not deleteriously affected by the presence of oxygen, however, perchlorate reduction was temporarily inhibited. Another potential problem with the bacteria used by Attaway and Smith (1993) is the requirement for high concentrations of proteinaceous nutrients such as nutrient broth and yeast extract. They state that this requirement can be met using aged brewers yeast, cottonseed protein or whey powder. The DM-17 and GR-1 isolates do not have this requirement and can reduce perchlorate using a minimal mineral medium such as BMS with acetate or succinate serving as the carbon source.

Herman and Frankenberger, Jr. (1999) isolated the bacteria they named perclace that was found to reduce perchlorate to levels less than 0.005 mg $L^{-1}$ when grown anaerobically on acetate. They described perclace as a gram negative, curved rod, facultative anaerobe that could reduce perchlorate or nitrate under anaerobic conditions. Gene sequencing using 16S rRNA methods indicated no similarity to any other sequenced bacteria, although they found a 90–92% sequence homology with several members of the β sub-division of Proteobacteria. Reduction of perchlorate was possible between 20–40° C., with an optimum of 25–30° C. Reduction of perchlorate occurred at pH 6.5–8.5, while the optimum pH was given as 7.0–7.2. These parameters closely match the optima and ranges for DM-17.

The Perlace isolate was also found to be able to use only oxygen, nitrate and perchlorate, but not Fe(III), Mn(IV), or sulfate, as electron acceptors. Using washed perclace cells, Herman and Frankenberger, Jr. (1999) found no difference in perchlorate reduction kinetics between aerobically and anaerobically grown cells. Using a 2.8 by 14 cm bioreactor column, they also found that perclace could reduce perchlorate levels below the State of California drinking water action level of 0.018 mg $L^{-1}$. Perchlorate reduction kinetics were rapid with 580 mg $L^{-1}$ of perchlorate reduced within a 72 h period.

Nzengung and Wang (1999) isolated four bacteria from the rhizoshere of willow trees and one was found to degrade perchlorate. The fastest degradation kinetics occurred at less than 100 mg $L^{-1}$ nitrate-N. The degradation kinetics also decreased with increasing nitrate concentration and was attributed to competing reactions where both anions were utilized as electron acceptors. They concluded that the exposure of rooted willow trees to perchlorate containing media stimulated the growth of perchlorate reducing bacteria in the rhizoshere. This finding suggests that the NARS system may have additional modes of perchlorate reduction besides sediment localized reactions.

Perchlorate can serve as a Terminal Electron Acceptor (TEA) due to its high oxidation state (+7). Coupled to an electron donor such as acetate, perchlorate and chlorate can be fully reduced to chloride ion by bacteria grown under anaerobic and microaerophilic conditions. Rikken et al. (1996) isolated a bacteria from activated sludge belonging to the β sub-division of Proteobacteria. Rikken et al. (1996) proposed the following pathway for the reduction of perchlorate:

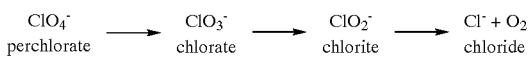

Attaway and Smith (1993) used a mixed enrichment culture derived from municipal anaerobic sludge. They found protein based media provided adequate carbon sources, but simple sugars, organic acids and alcohols were inadequate for perchlorate reduction. Adequate carbon sources included nutrient broth, yeast extract, casamino acids, and peptone. Perchlorate reduction was inhibited at concentration levels higher than 77.5 mM. Attaway and Smith (1993) also showed that perchlorate reduction was inhibited by oxygen and complete and permanent inhibition occurred when the culture was subjected to 12–24 h of aeration. This suggests the principal perchlorate reducing bacteria were strict anaerobes and required redox potential (Eh) less than −110 mV.

Giblin et al. (1999) found that an acetate based heterotrophic bioreactor using perclace was capable of reducing 500 mg $L^{-1}$ perchlorate to less than 5 $\mu$g $L^{-1}$ in 48 h (10.4 mg $L^{-1}h^{-1}$) at 30 ° C. They also studied a hydrogen-carbon dioxide gas based autotrophic system using a consortium of 5 organisms. The autotrophic system required 96 h to reduce 500 mg $L^{-1}$ perchlorate to less than 5 $\mu$g $L^{-1}$ (5.2 mg $L^{-1}h^{-1}$) at 30° C. Giblin et al. (1999) also found that both systems could simultaneously remove both perchlorate and 62 mg $L^{-1}$ nitrate.

Miller and Logan (2000) demonstrated high rates of perchlorate reduction using an autotrophic (hydrogen oxidizing) packed-bed biofilm reactor. The mixed consortium autotrophic culture contained the PRB known as Dechlorosoma sp. JM. Perchlorate reduction rates averaged 13.8 mg $L^{-1}$ $h^{-1}$ based upon a short detention time of 1.2 min. Another study using pressured hydrogen gas demonstrated a lower rate of reduction (1.02 mg $L^{-1}$ $h^{-1}$). The JM strain could reduce perchlorate using hydrogen, but required an organic carbon source for growth. The findings of Miller and Logan (2000) suggest that no single organism can be used in a hydrogen fed autotrophic bioreactor.

Although it is believed that the enzymes responsible for perchlorate reduction are linked to nitrate reductase enzymes systems, Wallace et al. (1996) found that Wolinella succinogenes (strain HAP-1) possessed a separate perchlorate reductase enzyme system. Their reasoning was based on the observation that HAP-1 did not lose its ability to reduce perchlorate in the presence of nitrate. However, in the case of chlorate reduction, Malmquist et al. (1994) suggests that Ideonella dechloratans possesses a modified nitrate reductase enzyme system.

From the patent literature such as Frankenberger, Jr. et al., cited above, and from the journal writings such as Coates et al. (1999), it is apparent that there continues to be a present and continuing need to discover and isolate new perchlorate and nitrate reducing microorganisms and to develop processes and systems for removing perchlorates and nitrates from materials such as soil and water using such organisms. It would further be desirable to identify substances that enhance the reduction of perchlorate and nitrate by perchlorate and nitrate reducing bacteria.

SUMMARY OF THE INVENTION

In accordance with one aspect of this invention, enhanced nitrate reduction has been accomplished with a mixed bacteria culture in the presence of perchlorate. In a preferred embodiment, the mixed bacteria culture is present in a marsh sediment. Preferably, the marsh sediment is collected at the influent end of the marsh. In one particular embodiment, the marsh at which the sediment was collected was the Arcata Marsh Pilot Project, Arcata, Humboldt County, California. This sediment was collected from the upper 5 cm. of cores taken from Cell 8 at the influent end of this marsh. In one preferred method, the sediment used to denitrify a material is pretreated by exposure to perchlorate over a period of time prior to contacting the sediment with material being treated.

Unlike Dendooven and Anderson (1994), the inventors observed a marked decline in nitrous oxide after 12 h. The decline in nitrous oxide may have been due to incomplete blockage by the acetylene blocking agent, allowing nitrous oxide to further reduce to nitrogen gas. Dendooven and Anderson (1995) also found that low nitrate concentrations resulted in incomplete blockage of nitrous oxide reduction.

In accordance with another aspect of the present invention, bacteria have been isolated that are particularly useful in the treatment of materials contaminated with perchlorate and/or nitrate. One bacterium is a gram-negative, motile, polymorphic bacterium isolated from sediment collected at the influent end (Cell 3) of the Arcata Marsh Pilot Project, Arcata, Humboldt County, California. Bacteria of this form have been given the name DM-17 and have been deposited at the American Type Culture Collection, Manassas, Va., under ATCC No. PTA-2685. The bacteria DM-17 exhibits both of the unexpected qualities mentioned above, which is to say, it reduces perchlorate and grows in so doing, and it is isolated from a marsh sediment not believed to have been exposed to perchlorate.

Further, a method for the removal of perchlorate and/or nitrate from the contaminated material has been developed in accordance with this invention that includes the treatment of the material with the bacteria DM-17. Materials that enhance perchlorate remediation have been discovered to be moderate levels of nitrate, and carbon sources. Cattail and molasses have been shown to be good carbon sources for this purpose.

Although the DM-17 isolate was capable of reducing perchlorate with acetate as the sole carbon source, it was observed that the combination of organic plant material (senesced Typha latifolia leaves) and molasses yielded very high reduction kinetics. t was determined that DM-17 could reduce perchlorate at the rate of 0.18 mM $h^{-1}$ (18 mg $L^{-1}$ $h^{-1}$) and 0.27 mM $h^{-1}$ (27 mg $L^{-}h^{-1}$), when incubated with 1 gm $L^{-1}$ and 5 gm $L^{-1}$ molasses, respectively. Although few studies have provided kinetic data, these rates are high in comparison to other autotrophic and heterotrophic systems.

Additionally, in accordance with the invention improved perchlorate remediation of a contaminated material includes contacting the material with the bacteria DM-17 in the presence of nitrate. Preferably, the bacteria DM-17 metabolizes both the perchlorate contaminants and nitrates in the contaminated material.

The inventors determined that the DM-17 isolate can reduce perchlorate in the presence of nitrate, but levels above 10 mM (620 mg $L^{-1}$ nitrate or 140 mg $L^{-1}$ nitrate-N) significantly inhibit perchlorate reduction. Other authors have discussed the need to first remove or reduce the nitrate loading of waste feeds to perchlorate bioreactors. Most studies investigating inhibitory effects of nitrate focused on levels far lower than the levels the inventors studied. For instance, Giblin et al. (2000) used 26 mg $L^{-1}$ nitrate (equivalent to 5.9 mg $L^{-1}$ nitrate-N) in their heterotrophic bioreactor. Herman and Frankenberger, Jr. (1999) found that perclace was unaffected when nitrate and perchlorate were equimolar. However, when the molar concentration of perchlorate was 10, 100, or 1,000 times lower than nitrate, perchlorate reduction was inhibited. The maximum nitrate concentration tested was 1 mM (62 mg $L^{-1}$ nitrate or 5.9 mg $L^{-1}$ nitrate-N). Herman and Frankenberger, Jr. (1999) also found that perchlorate breakthrough occurred when a bench scale sand-packed column received both 125 and 20 mg $L^{-1}$ nitrate. Logan et al. (1999), while discussing bioreactor design considerations, points to the need to first remove nitrate from the waste stream.

Preferably, the DM-17 bacteria are used to reduce both the perchlorate and nitrate where contaminated material includes both contaminants. This ability permits the DM-17 bacteria to sustain itself in the absence of perchlorates and be effective in the reduction of perchlorate, where for example, nitrate remediation is ongoing and perchlorate appears sporadically in the material being remediated.

Also, in accordance with the present invention, a biologically pure culture of the bacteria that has been identified as DM-17 has been produced.

Although the bacteria isolated in accordance with the invention will thrive in an anaerobic environment on perchlorate, a complete absence of oxygen is not essential to perchlorate reduction.

The above and further features of the invention will be better understood with reference to the accompanying drawings taking in consideration with the following detailed description of a preferred embodiment.

Figure 1:
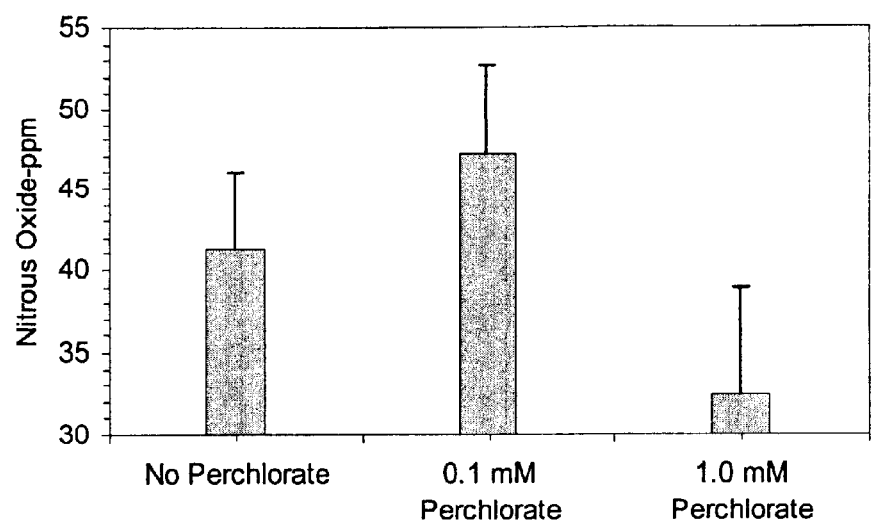
FIG. 1 is a graphical comparison of the effects of a mixed culture bacterial treatment of sediment having no known previous exposure to perchlorate in the presence of no perchlorate, a moderate level of perchlorate, and a high level of perchlorate and plots the resultant nitrous oxide content of treated sediment in each case.

A culture of purified bacteria DM-17 isolated from marsh sediment was deposited on Nov. 16, 2000 with the American Type Culture Collection (hereinafter "ATCC") and accepted in accordance with the provisions of the Budapest Treaty on the International Recognition of the Deposit Microorganisms for the Purpose of Patent Procedure. The ATCC is located at 10801 University Boulevard, Manassas, Va. 20110–2209 U.S.A. The deposited bacteria was assigned ATCC Designation No. PTA-2685. For purposes of this disclosure, the bacteria deposited with the ATCC and designated ATCC Designation No. PTA-2685 is hereby incorporated by reference. All restrictions imposed by the depositor on the availability to the public of the deposited biological material will be irrevocably removed upon the granting of the patent.

DETAILED DESCRIPTION

Perchlorate Effect on Denitrification

The effect of perchlorate on bacterial denitrification was initially investigated. This was done with sediment not previously known to have been exposed to perchlorate either in the environment or in the laboratory and also with sediment preconditioned in the laboratory by exposure to perchlorate.

Methods and Materials

Unconditioned Sediment Study

Sediment cores were collected from Cell 8 of the Arcata Marsh Pilot Project (AMPP), Arcata, Humboldt County, California. These were believed to have no previous environmental exposure to perchlorate. Samples were collected using a 5.7 cm diameter lexan coring device. Multiple cores (upper top five cm) of sediment were collected and immediately placed in sterile polyethylene plastic ziplock bags, evacuated of residual air and sealed. Samples were transported to the lab within 0.5 h and placed on ice. Within 45 min., a composite sediment sample was forced through a 457 $\mu$m sieve with enough deionized water to create a homogenized slurry.

While mixing on a stir-plate, 4 mL of sediment slurry was added to each test vial. Pre-cleaned 40 mL clear borosilicate vials with 0.125" PTFE septa liners were used. The vials were held in an ice bath during the addition of the sediment slurry and a culture medium to minimize any biochemical reactions. The culture medium that each vial received was a defined minimal culture medium containing 60 mM potassium acetate and 100 $\mu$M potassium nitrate. Experimental treatment vials also received either 0.1 mM or 1.0 mM potassium perchlorate (A.C.S. reagent grade, Spectrum Quality Products, Inc., Gardena, Calif.). The total volume of culture medium added to each vial was 10 mL.

Experimental treatments consisted of the following: no perchlorate/acetylene, 0.1 mM perchlorate/acetylene, 1.0 mM perchlorate/acetylene, no perchlorate/no acetylene, and 0.1 mM perchlorate/no acetylene. Acetylene is known to block the final step of reduction of nitrous oxide to nitrogen in bacterial treatment. Time zero ($t_0$) controls with no perchlorate/no acetylene were also included. Each treatment, with the exception of the $t_0$ controls, consisted of 10 replicates. The $t_0$ controls consisted of five replicates. All vials were distributed in a randomized block design.

Imediately following the addition of reagents, the vials were capped and sealed. While remaining in an ice bath, each vial was sparged with pre-purified nitrogen gas for two min. to remove residual oxygen. Approximately 3 mL of acetylene was then added to each vial requiring the blocking agent. Acetylene gas was prepared using a calcium carbide acetylene generator. All acetylene additions were completed within 25 min. The timing of the experiment began immediately after all vials received acetylene and were removed from the ice water bath. The $t_0$ controls vials were fixed with 1.0 mL of 5 N sulfuric acid. All vials were incubated at 25° C. for 23.5 h until fixation with 5 N sulfuric acid. All samples were analyzed for nitrous oxide within 24 h of fixation.

Perchlorate Conditioned Sediment Study

From the sediment collected, sediment slurry was prepared as described in the preceding section. Perchlorate conditioned sediment was prepared by placing approximately 100 mL of slurry, described above, into an air tight one-liter bioreactor and adding as a culture medium, a solution containing 60 mM potassium acetate, 100 $\mu$M potassium nitrate and 1.0 mM potassium perchlorate. An unexposed control was treated identically, but did not include perchlorate. The total volume of sediment slurry culture in each bioreactor was one liter. Bioreactors were sparged for 20 min. with nitrogen gas. Cultures were incubated at 25° C. After 5 d, the solution was removed and discarded. Fresh solution was added to the sediment to prevent senescence and aging of bacteria reactors were sparged for 20 min. and replaced in the incubator at 25° C. Following an additional 24 h incubation, the solutions from each container were removed by aspiration and replaced with deionized water.

All treatments and subsequent steps prior to analysis of nitrous oxide were as described in the preceding section. All vials received acetylene within 25 min. of each other. Vials were incubated for 21 h, after which all were fixed with 0.5 mL of 5 N sulfuric acid. All vials were analyzed for nitrous oxide within 7 h of fixation.

Kinetics Study

Perchlorate conditioned sediment described in the preceding section was amended with 5% (v/v) untreated marsh sediment slurry. The mixed culture was sparged for 20 min. and allowed to settle in an incubator for 5 h at 25° C. Following the removal of supernatant, the sediment received one liter of fresh culture medium containing 60 mM potassium acetate, 100 $\mu$M potassium nitrate and 1.0 mM perchlorate. The bioreactor was sparged and incubated at 25° C. At 48 h, an additional 0.5 mL of 100 mM potassium perchlorate was added to the perchlorate treated sediment. The solutions were exchanged after 6 d with fresh culture medium, as described above, sparged and incubated at 25° C. The solutions were exchanged after 14 d with medium containing 60 mM potassium acetate, 100 $\mu$M potassium nitrate and 0.1 mM perchlorate, then sparged and incubated at 25° C. for one additional week. No perchlorate was added to the control sediment.

The supernatant was aspirated from the reactor after 21 d and replaced with 250 mL of deionized water. While stirred, 2 mL of slurry was removed and added to each test vial. The slurry in each vial received 10 mL of culture medium containing 60 mM potassium acetate, 100 $\mu$M potassium nitrate and 0.1 mM perchlorate. Controls were treated identically to the treatments except no perchlorate was added.

Within 1 h, each vial was sparged with pre-purified nitrogen gas for 1 minute and incubated at 25° C. After 5 d, the solution from each vial was aspirated and replaced with 10 mL of fresh culture medium containing 60 mM potassium acetate, 100 $\mu$M potassium nitrate and 0.1 mM potassium perchlorate. Controls were treated identically to the treatments except no perchlorate was added.

Experimental treatments consisted of the following: 0.1 mM perchlorate/acetylene, 0.1 mM perchlorate/no acetylene, no perchlorate/acetylene, and no perchlorate/no acetylene. Time zero ($t_0$) controls with no perchlorate/no acetylene were also included. Each treatment consisted of two replicates. However, the $t_0$ controls consisted of three replicates. All vials were distributed in a randomized block design.

All vials were sparged within one hour after receiving new culture media and were maintained on ice. Selected vials were injected with acetylene within 30 min. of sparging. Time zero controls were fixed immediately after acetylene addition with 0.5 mL of 5 N sulfuric acid. Other vials were fixed hourly from 1–8 h, then at 10, 12 and 25 h. Two replicates were analyzed for each treatment. All vials were analyzed for nitrous oxide by gas chromatography within 30 h of fixation.

Nitrous Oxide Analysis

Throughout these experiments, nitrous oxide ($N_2O$) was analyzed using a gas chromatograph (model GC-14A, Shimadzu Co., Tokyo, Japan) equipped with a $^{63}Ni$ electron capture detector (300° C.). Gases were separated on a 6'×⅛" stainless steel column packed with 50/80 mesh Porapak N (270° C.) and integrated (Chromatopac integrator, model C-R5A, Shimadzu Co., Tokyo, Japan). The carrier gas was ultra high purity nitrogen gas (Air Liquide, Houston, Tex.). A series of $N_2O$ standards (100 ppm nitrous oxide, Scotty I, Scott Specialty Gases, Inc.) were analyzed between each set of replicates. Each vial was first shaken to equilibrate the gas and liquid phases, then 300 µL of headspace was sampled using a gas-tight syringe (Hamilton Company, Reno, Nev.) and injected into the GC. Each vial was sampled and analyzed in duplicate. The concentration of $N_2O$ in the water phase was calculated by:

$$C^* = K_0 f$$

Where:

$C^*$ = concentration in water phase (moles $L^{-1}$)

$K_0$ = equilibrium constant (mole L−1 $atm^{-1}$)

f = fugacity of $N_2O$ (approximately equal to concentration of $N_2O$ in gas phase in units of $N_2O$ per volume of total gas).

Molar equivalents in the water and gas phase were combined to yield a single net production of $N_2O$.

Results

Unconditioned Sediment Study-Results

This study was to investigate the potential of perchlorate to interfere with normal denitrification processes using the unconditioned marsh sediment (previously unexposed to perchlorate), two levels of perchlorate (0.1 and 1.0 mM) and a control (0 mM perchlorate). All groups received 100 µM potassium nitrate. The effect of perchlorate on denitrification using marsh sediment unconditioned by perchlorate is shown in FIG. 1. The data points shown in FIG. 1 are mean nitrous oxide measurements (ppm±2 SE, n=10). All treatments received acetylene blocking agent. Surprisingly, the experiment showed that denitrification was inhibited by perchlorate only when the concentration of perchlorate was relatively high. See Table 1. In fact, the 0.1 mM perchlorate treatment produced 14.0% more nitrous oxide compared to the control without perchlorate, while the 1.0 mM perchlorate treatment produced 22.0% less nitrous oxide compared to the control. Analysis of Variance (ANOVA) indicated statistical difference between treatments and control (p=0.0001, two tailed). Duncan's Multiple Comparison confirmed that relatively high perchlorate levels (1.0 mM) inhibited denitrification and moderate perchlorate levels (0.1 mM) slightly stimulated denitrification. In treatments without added acetylene (i.e., no nitrous oxide reductase blocking agent), results indicated that 0.1 mM perchlorate also enhanced denitrification (p=0.00015, two tailed).

TABLE 1

Mean (ppm) and 95% confidence limits of measured nitrous oxide produced by unconditioned marsh sediment.

| n = 10 | No $ClO_4^{-1}$ (ppm) | 0.1 mM $ClO_4^{-1}$ (ppm) | 1.0 mM $ClO_4^{-1}$ (ppm) |
|---|---|---|---|
| Mean | 41.4 | 47.2 | 32.3 |
| 95% LCL | 36.7 | 41.6 | 25.7 |
| 95% UCL | 46.0 | 52.7 | 39.0 |

Perchlorate Conditioned Sediment Study-Results

Following up on the preceding results, this study was to investigate the potential of perchlorate to interfere with normal denitrification processes using perchlorate-conditioned marsh sediment (6 d exposure to 1 mM potassium perchlorate), two levels of perchlorate (0.1 and 1.0 mM) and a control (0 mM perchlorate). All groups received 100 µM potassium nitrate.

Figure 2:
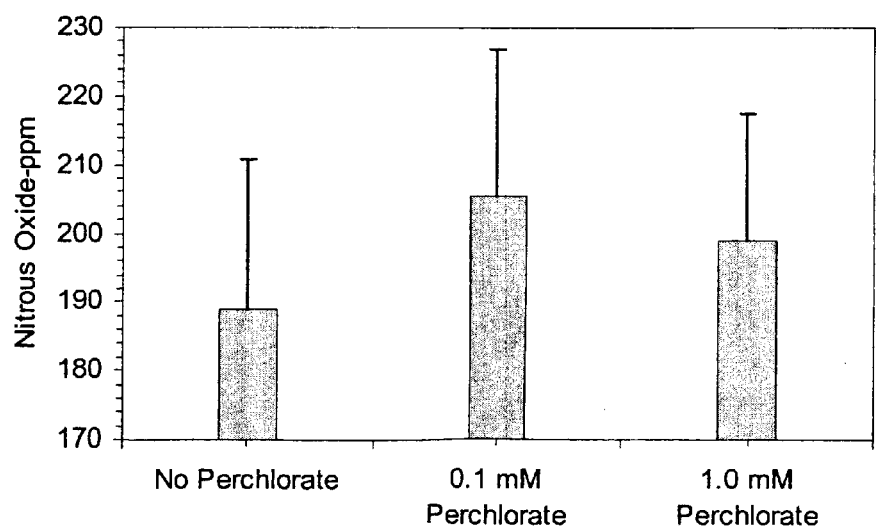
FIG. 2 is a graphical comparison like FIG. 1 and plots the resultant nitrous oxide content produced from sediment after contact by a mixed culture having laboratory conditioning to perchlorate.

Conditioned inoculant showed no inhibition of denitrification in the presence of perchlorate (Table 2). FIG. 2 illustrates the effect of perchlorate on denitrification using marsh sediment inoculant pre-conditioned with 1.0 mM perchlorate. Data points shown are mean nitrous oxide measurements (ppm±2 SE, n=10). All treatments received acetylene blocking agent. The 0.1 mM and 1.0 mM perchlorate treatments produced 9.0% and 5.3%, respectively, more nitrous oxide compared to the control without perchlorate. ANOVA indicated statistical difference between treatments and control (p=0.0009, two-tailed). Duncan's Multiple Comparison Test indicated that both the 0.1 mM and 1.0 mM perchlorate treatments stimulated or accelerated denitrification. Treatments without added acetylene also indicated that 0.1 mM perchlorate enhanced denitrification (p<0.00001, two-tailed). In the absence of acetylene, 0.1 mM perchlorate produced very little nitrous oxide indicating acceleration of the nitrous oxide reductase mediated step.

TABLE 2

Mean (ppm) and 95% confidence limits of measured nitrous oxide produced by perchlorate conditioned marsh sediment.

| n = 10 | No $ClO_4^{-1}$ (ppm) | 0.1 mM $ClO_4^{-1}$ (ppm) | 1.0 mM $ClO_4^{-1}$ (ppm) |
|---|---|---|---|
| Mean | 189 | 206 | 199 |
| 95% LCL | 167 | 184 | 181 |
| 95% UCL | 211 | 227 | 218 |

Kinetics Study-Results

Figure 3:
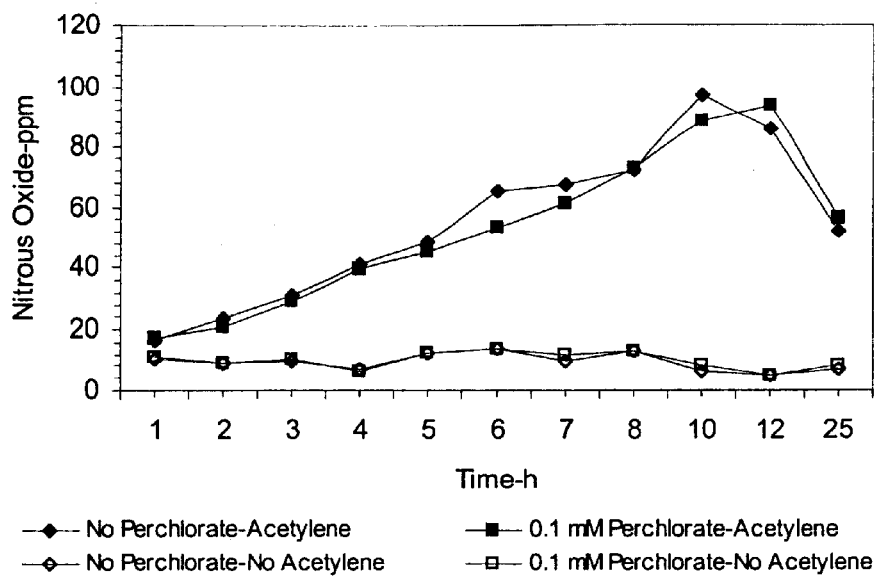
FIG. 3 is a plot of resultant nitrous oxide versus incubation time for denitrification with a mixed culture with no perchlorate, but acetylene present, with perchlorate and acetylene present, with no perchlorate and no acetylene present, and with perchlorate and no acetylene present.

This experiment specifically designed to measure the kinetics of denitrification using pre-conditioned marsh sediment showed that perchlorate primarily had an effect on denitrification by slightly delaying the nitrous oxide peak (Table 3). FIG. 3 illustrates the effect of perchlorate on denitrification using the marsh sediment inoculant pre-conditioned with 1.0 mM perchlorate. Data points shown are mean nitrous oxide measurements (ppm, n=2). The nitrous oxide peak of the control containing no perchlorate occurred at 10 h, while the peak of the treatment occurred at 12 h. Regression analysis indicated denitrification rates of 0.016 µM $N_2O$ $vial^{-1}h^{-1}$ (no perchlorate) and 0.0145 µM $N_2O$ $vial^{-1-1}$ (0.1 mM perchlorate). However, F-Test comparisons indicated no significant difference (p=0.54, two-tailed) in the kinetic rates. The vials without acetylene demonstrated a very similar pattern, indicating no qualitative effect of 0.1 mM perchlorate on the final conversion of nitrous oxide to nitrogen gas.

TABLE 3

Measured nitrous oxide produced by perchlorate conditioned marsh sediment.

| Time (h) | No $ClO_4^{-1}$ With Acetylene (ppm) | 0.1 mM $ClO_4^{-1}$ With Acetylene (ppm) | No $ClO_4^{-1}$ No Acetylene (ppm) | 0.1 mM $ClO_4^{-1}$ No Acetylene (ppm) |
|---|---|---|---|---|
| 1 | 16.5 | 17.4 | 10.4 | 11.0 |
| 2 | 23.4 | 20.5 | 8.8 | 8.9 |
| 3 | 31.2 | 28.9 | 9.6 | 10.6 |
| 4 | 40.8 | 39.7 | 6.7 | 6.5 |
| 5 | 48.9 | 45.1 | 12.7 | 12.5 |
| 6 | 65.3 | 53.5 | 13.9 | 13.6 |
| 7 | 67.5 | 61.2 | 9.8 | 11.9 |
| 8 | 72.0 | 73.1 | 13.0 | 13.3 |
| 10 | 96.9 | 87.9 | 6.6 | 8.5 |
| 12 | 85.2 | 93.7 | 5.0 | 4.6 |
| 25 | 51.7 | 56.2 | 7.1 | 8.0 |

Enrichment, Isolation and Characterization of Perchlorate Reducing Bacteria

Culture Enrichment

Enrichment of perchlorate reducing bacteria (PRB) initially used inoculate derived from wastewater treatment marsh sediment. Sediment cores were collected from Cell 3 (influent end) of the AMPP. Sediment samples were collected using a 5.7 cm diameter lexan coring device. Multiple cores (upper top five cm) were collected and immediately transferred to a sterile ziplock bag, evacuated and sealed. The sediment was transported to the lab and immediately homogenized through a 457 μm sieve with deionized water to create a uniform slurry.

The enrichment medium contained the following: monobasic potassium phosphate momohydrate, 6 g $L^{-1}$; dibasic potassium phosphate, 2 g $L^{-1}$; potassium perchlorate, 1.3855 g $L^{-1}$; potassium acetate trihydrate, 5.88 g $L^{-1}$, and resazurin, 1 mg $L^{-1}$. Culture medium in 1 L bioreactors was sparged with nitrogen gas after sterilizing, then inoculated with 10% (v/v) sediment slurry. Culture vessels were incubated at 28° C. for 35 d.

Following an initial enrichment period, the culture was transferred to a basal mineral salts (BMS) medium containing the following: monobasic sodium phosphate monohydrate, 36 mg $L^{-1}$; dibasic potassium phosphate, 128 mg $L^{-1}$; sodium acetate trihydrate, 13.61 g $L^{-1}$; potassium perchlorate, 1.38 g $L^{-1}$, ammonium chloride, 60 mg $L^{-1}$; sodium nitrate, 85 mg $L^{-1}$; magnesium sulfate heptahydrate, 10 mg $L^{-1}$; calcium chloride dihydrate, 10 mg $L^{-1}$; ferrous sulfate heptahydrate, 2.8 mg $L^{-1}$; resazurin, 1 mg $L^{-1}$; and 1 mL $L^{-1}$ of trace metals solution (Herman and Frankenberger, Jr., 1999). The trace metals solution was made containing the following trace metals: 1 mM boric acid, 1 mM manganous sulfate, 1 mM zinc sulfate heptahydrate, 1 mM copper sulfate, 0.1 mM nickel sulfate, 0.1 mM cobalt sulfate, and 0.1 mM sodium molybdate dihydrate (Focht, 1994). Culture vessels were incubated anaerobically for 6 d at 28° C.

Solid BMS plates (15 g $L^{-1}$ agar) were prepared for isolating single bacterial types growing in broth culture. Streak plates were grown at 30° C. both aerobically and within an air evacuated anaerobic chamber. Single isolates were transferred back to perchlorate containing BMS broth to quantify perchlorate reducing performance. Once an isolate was confirmed as a perchlorate reducing bacteria, it was grown and maintained on PSS medium (Bergey's Manual, 1984). The PSS medium was prepared with: Bacto peptone (Difco), 10 g $L^{-1}$; succinic acid, 1.0 g $L^{-1}$; ammonium sulfate, 1.0 g $L^{-1}$; magnesium sulfate heptahydrate, 1.0 g $L^{-1}$; ferric chloride, 2 mg $L^{-1}$; manganese sulfate monohydrate, 2.0 mg $L^{-1}$; trace metals solution, 1 mL $L^{-1}$: (Focht, 1994); and 15 g $L^{-1}$ agar. The pH was adjusted to pH 7.0 prior to autoclaving using 10 M potassium hydroxide.

Bacterial Gene Sequencing

A single isolate recovered from the enrichment culture was sent to MIDI Labs (Newark, Del.) for partial (500 bp)16S rRNA gene sequencing. As a follow up, a second culture was sent to MIDI Labs for full (1500 bp)16S rRNA gene sequencing. The biologically pure isolate was given the name DM-17. It has been deposited with the American Type Culture Collection (ATCC), Manassas, Va., on Nov. 16, 2000, by the Humboldt State University Foundation, preliminarily identified as strain DM-17 of either Azoarcus sp. or *Dechlorosoma suilla,* isolated from wetland wastewater treatment system Arcata, Calif. (Humboldt County), now ATCC Deposit No. PTA-2685. "Biologically pure" as used herein refers to the DM-17 bacteria once it has been separated from its naturally occurring surroundings, i.e. sediment.

The 16S rRNA gene was PCR amplified from genomic DNA isolated from supplied bacterial colonies. Primers used for the amplification correspond to *E. coli* positions 005 and 1540 (full-length sequence) and 005 and 531 (500 bp sequence). Amplification products were purified with Microcon 100 (Amicon) molecular weight cut-off membranes.

Cycle sequencing of the 16S rRNA amplification products was performed using AmpliTaq FS DNA polymerase and dRhodamine dye terminators. Excess dye-labeled terminators were removed from the sequencing reactions using a Sephadex G-50 spin column. The products were collected by centrifugation, dried under vacuum and frozen at −20° C. until ready to load. Samples were resuspended in a solution of formamide/blue dextran/EDTA and denatured prior to loading. The samples were electrophoresed on a ABI Prism 377 DNA Sequencer and data was analyzed using PE/Applied Biosystems DNA editing and assembly software. Both the MicroSeq and GenBank databases were used for determining sequence identities.

Isolation and Characterization of Perchlorate Reducing Bacteria

Isolation and Enrichment

The perchlorate reducing isolate (DM-17) was successfully recovered from the marsh sediment by enriching a culture using a defined basal mineral salts medium containing 10 mM potassium perchlorate and grown at 25° C. as described. After the second enrichment at 25° C., perchlorate levels dropped below probe detection (<10 μM or 1 mg $L^{-1}$) within one week. The culture consisted primarily of gram negative motile rods. The second culture was plated on solid BMS medium and solid PSS medium.

The dominant form growing on solid BMS medium were small clear-white, pinhead-sized colonies observed after 48 h of growth. Microscopic examination revealed that the isolate was a gram-negative motile rod showing little or no curvature. A representative colony was chosen from the BMS plate and used to inoculate BMS broth containing 10 mM perchlorate and incubated at 25° C. Perchlorate was fully reduced after 7 d of incubation. During the growth phase of the isolate, the resazurin redox indicator was light pink, indicating slightly oxidized conditions (Eh>−110 mV). It was noted that the resazurin indicator color change from pink to clear coincided with perchlorate levels below detectable levels.

Identification of Bacterial Isolate DM-17

The partial 500 bp 16S rRNA gene sequencing indicated that the DM-17 isolate could not be matched to any known species. Within the MicroSeq database, the closest match was *Aquaspirillum autotrophicum* (91.4% match). However, a search of the GenBank database indicated a preliminary match (100% identity, 521/521) with *Dechlorosoma suilla* (AF170348), a novel bacterium described by Coates et al. (1999) as belonging to the β subdivision of Proteobacteria. The GenBank database also indicated 100% identity (481/481 bp matches) with Azoarcus sp. (strain BS2-3, AF011351).

A second attempt at identifying the DM-17 isolate using full length (1500 bp) 16S rRNA sequencing indicated the closest match within the MicroSeq database was *Ralsonia eutropha* (91.8% gene homology). Again, a search of the GenBank database indicated an excellent match (99.8% identity, 1529/1532 bp matches) with *D. suilla*. An excellent match was also found between DM-17 and Azoarcus sp. (strain BS2-3, AF011351) indicated by 100% identity (1435/1435 bp matches). Thus, at this time it is concluded that the DM-17 isolate is most genetically similar to either Azoarcus sp. or the novel bacteria described by Coates et al. (1999) as *D. suilla*.

Isolate Characterization

Partial biochemical characterization showed that the DM-17 isolate could utilize acetate and succinate, but not citrate, as carbon sources. The isolate was weakly catalase positive, cytochrome C-oxidase positive, was inhibited by 3% sodium chloride, could grow both aerobically and anaerobically, and could denitrify. The DM-17 isolate also could not utilize Fe(III) or $SO_4^{2-}$ as electron acceptors. When grown on solid BMS medium, growth was typically more luxuriant when grown anaerobically rather than aerobically.

The DM-17 isolate grown in broth culture displayed polymorphism. Under some environmental conditions, the dominant form was a long motile helical rod. Replating the atypical cultures verified the same morphology as DM-17. It was noted that the polymorphism was much more apparent when grown at cooler temperatures (20° C.), with the dominant form having up to six helical turns and a length up to 20 μM. Under normal growing conditions and warmer incubation temperatures (30° C.), the dominant morphology was 0.3 μm×2 μm. When viewed with phase contrast microscopy, the bacteria showed rapid bi-directional motion.

Figure 4:
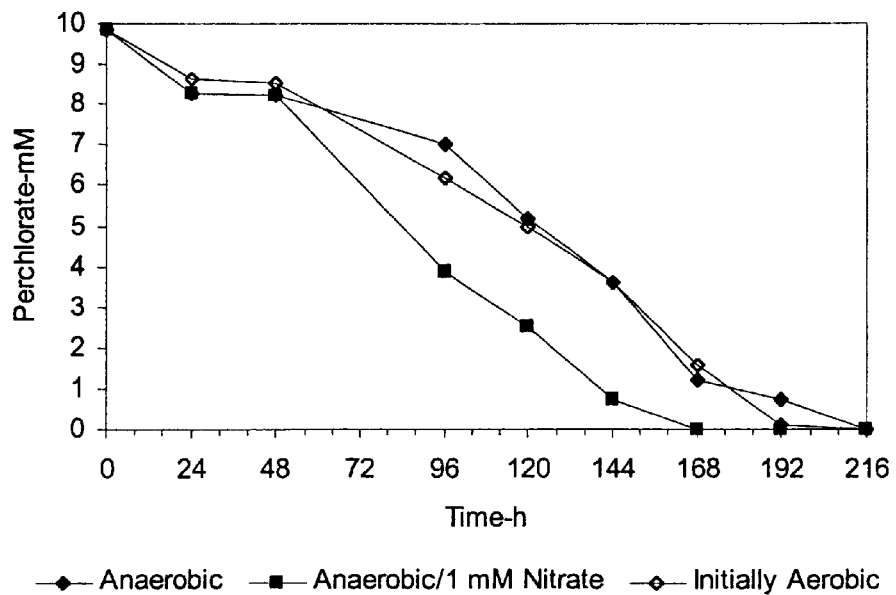
FIG. 4 is a plot of perchlorate versus incubation time for bacterial perchlorate remediation by the DM-17 bacteria and compares anaerobic treatment in the absence of nitrate, anaerobic treatment in the presence of nitrate, and initially aerobic treatment in the absence of nitrate.

It was earlier observed that the combination of perchlorate and nitrate may enhance the rate of denitrification. Therefore, an experiment was designed to determine the converse, that is if nitrate could accelerate the rate of perchlorate reduction. As shown in Table 4 and FIG. 4, 1.0 mM sodium nitrate improved the kinetics of perchlorate reduction. FIG. 4 illustrates the effect of 1.0 mM nitrate on perchlorate reduction by isolate DM-17. Data points are single measurements. At 4 d, the nitrate and non-nitrate containing cultures reduced the initial perchlorate level by 60.9% and 28.9%, respectively. At 6 d, the nitrate and non-nitrate containing cultures reduced the initial perchlorate level by 92.6% and 63.2%, respectively. The rate of perchlorate reduction was slightly improved for the nitrate containing culture (77.3 μM $h^{-1}$) compared to the non-nitrate containing culture (47.4 μM $h^{-1}$).

TABLE 4

Effect of 1.0 mM nitrate on perchlorate reduction by isolate DM-17.

| Incubation (d) | Anaerobic (mM) | Anaerobic 1 mM Nitrate (mM) | Initially Aerobic (mM) |
|---|---|---|---|
| 0 | 9.86 | 9.86 | 9.86 |
| 1 | 8.27 | 8.27 | 8.63 |
| 2 | 8.20 | 8.20 | 8.55 |
| 4 | 7.01 | 3.86 | 6.17 |
| 5 | 5.20 | 2.53 | 4.98 |
| 6 | 3.63 | 0.73 | 3.63 |
| 7 | 1.21 | <0.01 | 1.55 |
| 8 | 0.72 | <0.01 | 0.11 |
| 9 | <0.01 | <0.01 | <0.01 |

A third culture was allowed aerobic growth for the first 48 h and then was sealed and allowed to grow anaerobically. The aerobic culture showed a rate of reduction of 50.9 μM $h^{-1}$, indicating a very similar rate as the anaerobic culture. By day eight, the aerobic and anaerobic culture without added nitrate showed 98.9% and 92.7% reduction, respectively, while the nitrate containing culture showed 99.9% reduction.

Figure 5:
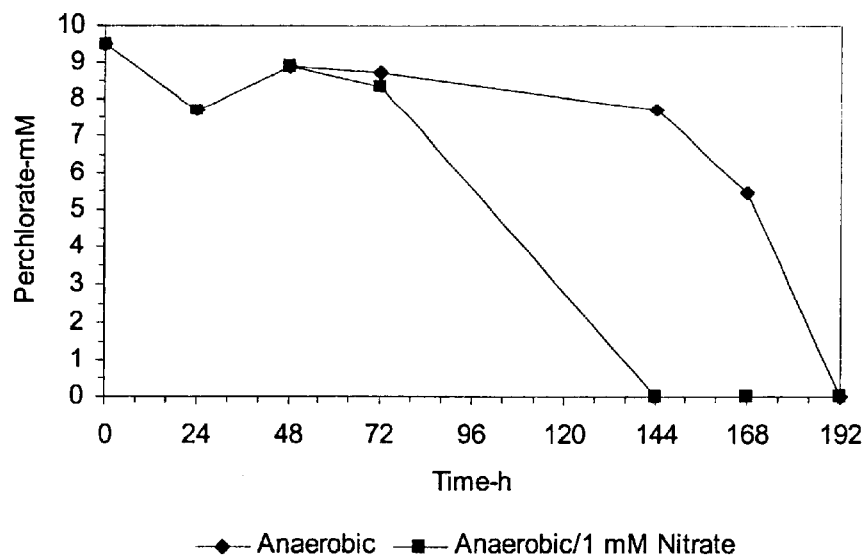
FIG. 5 is a further plot of perchlorate versus incubation time and compares anaerobic perchlorate remediation with the DM-17 bacteria with and without nitrate present.

Another experiment was performed to verify the effect of nitrate on perchlorate reduction. FIG. 5 shows that in the presence of 1.0 mM sodium nitrate in the BMS medium, perchlorate reduction by DM-17 was dramatically accelerated during the first 6 d. Data points are single measurements. Within 6 d, greater than 99.9% of the initial perchlorate was reduced in the presence of 1.0 mM nitrate, while only 19.4% was reduced in the absence of nitrate. Both cultures showed perchlorate levels less than detectable (<10 μM) within 8 d.

Figure 6:
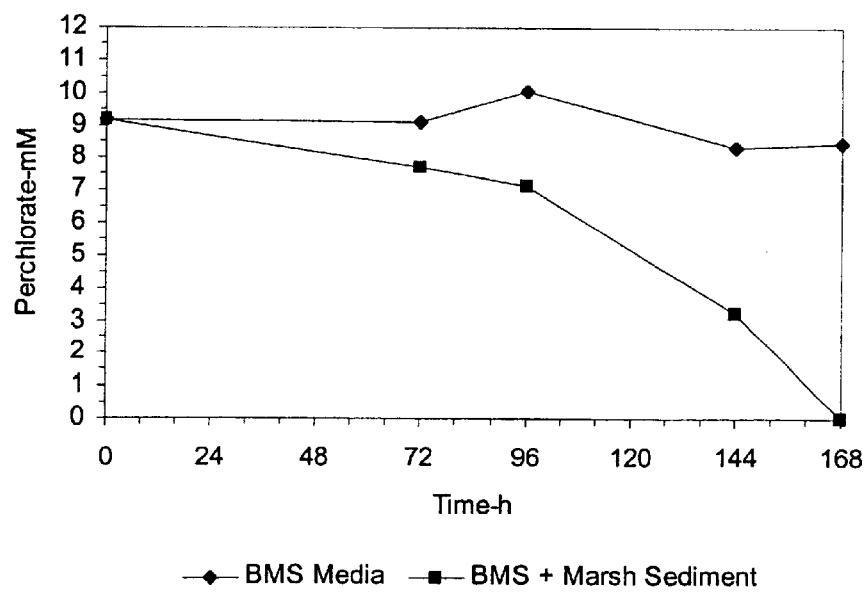
FIG. 6 is a plot of perchlorate versus incubation time and compares perchlorate reduction by the DM-17 bacteria in a basal metal salt enrichment medium (BMS) alone and with sediment.

It was previously noted that cultures without added trace metals or without added marsh sediment resulted in slow growing cultures. Thus, an experiment was designed to determine if the culture could be aided by adding autoclaved marsh sediment. Prepared trace metals were excluded from all media. FIG. 6 illustrates the effect of added marsh sediment on perchlorate reduction by isolate DM-17 using the BMS culture medium. Data points are single measurements. It shows that without added marsh sediment the isolate grows poorly in the presence of 10 mM sodium perchlorate and 2 mM sodium nitrate. In contrast, the culture with added marsh sediment reduced perchlorate more than 99.9% (<10 μM) within 7 d. The culture without added marsh sediment reduced perchlorate by 8.0% within 9 d.

Figure 7:
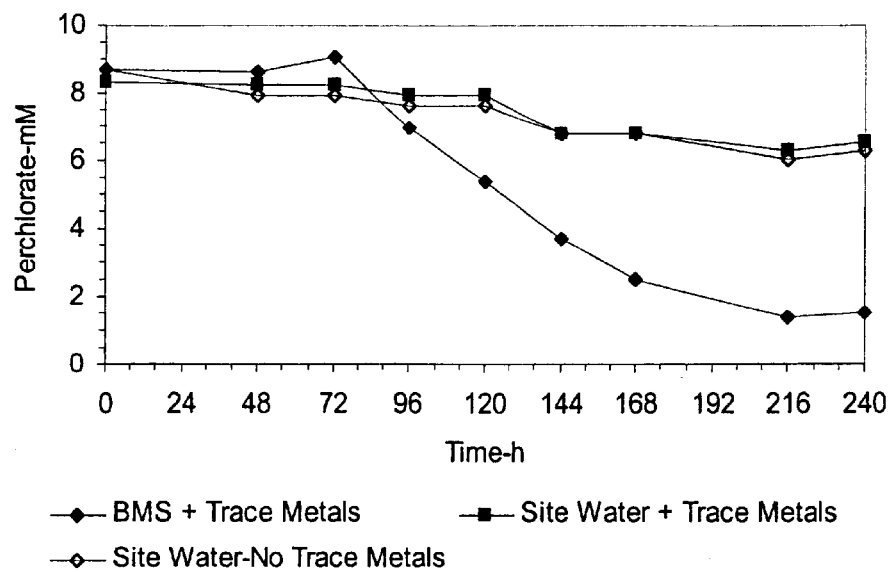
FIG. 7 is a plot of perchlorate versus incubation time and compares perchlorate reduction by the DM-17 bacteria in the presence of the enrichment medium (BMS) and trace metals, site water and trace metals and site water and no trace metals.
Figure 8:
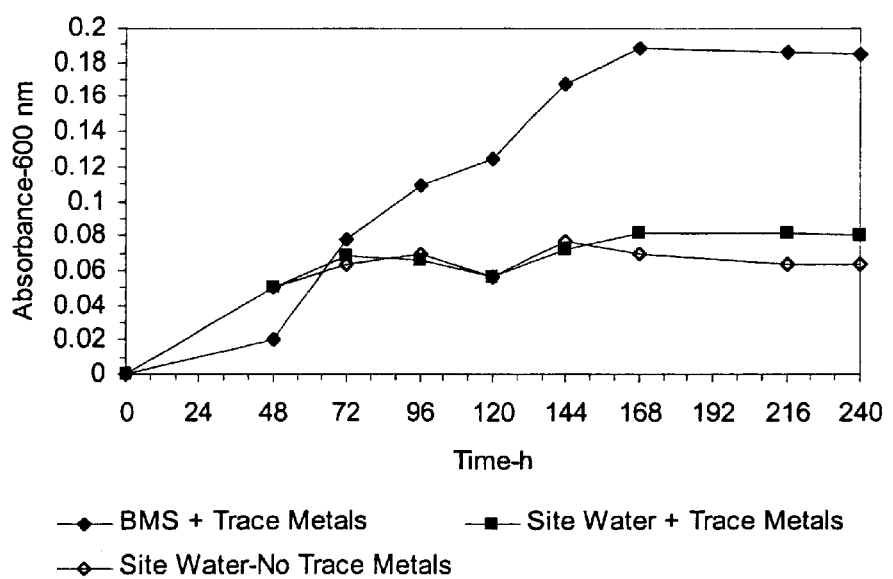
FIG. 8 is a plot of growth rate (absorbance at 600 nm) versus incubation time of the DM-17 bacteria in BMS medium with trace metals, site water and trace metals and site water with no trace metals.

To determine if the DM-17 isolate could grow in site water collected from the APSS with added sodium acetate (100 mM), an experiment was designed to compare perchlorate reduction rates between BMS medium and site water (SEW-1). The site water treatment was further divided into site water with and without trace metals. FIG. 7 illustrates perchlorate reduction by isolate DM-17 using BMS medium and site water prepared with and without trace metals. All media contained 100 mM sodium acetate. Data points are single measurements. It shows substantial difference between the culture grown in BMS medium and the cultures grown in site water. Site water treatments, both with and without trace metals, yielded a very similar temporal pattern indicating that the reason for the poor performance was independent of trace metals. The perchlorate reduction rates for the BMS medium, site water with trace metals and site water without trace metals were 68.0 μM $h^{-1}$, 17.8 μM $h^{-1}$ and 13.5 μM $h^{-1}$, respectively. FIG. 8 illustrates growth rate (absorbance at 600 nm) of isolate DM-17 growing in BMS medium and site water (SEW-1) prepared with and without trace metals. All media contained 100 mM sodium acetate. Data points are single measurements. FIG. 8 shows that the isolate growth rate was substantially better in the prepared BMS medium.

DM-17 Isolate Performance
Redox (Eh) and Low Level Perchlorate Removal

An experiment was set up using a 2 L bioreactor with an internally mounted in-situ redox electrode to measure redox potential (Eh) during active perchlorate reduction. The BMS medium was prepared with 10 mM sodium perchlorate and 100 mM sodium acetate. The reactor was inoculated with DM-17 previously grown aerobically on PSS. Single measurements of perchlorate, chloride, absorbance (600 nm), redox and pH were taken daily. Following sample removal from the reactor, the headspace was purged with nitrogen gas.

Following the determination that perchlorate measurements were below the electrode limit of detection (LOD), samples were removed for low level perchlorate analysis by Montgomery-Watson Laboratories (MWL). Approximately 100 mL of sample was placed in 125 mL pre-cleaned polyethylene sample bottles supplied by MWL. The pH of each sample was reduced to 4.5 using concentrated sulfuric acid to inhibit bacterial reduction of any remaining perchlorate.

Inhibitory Effects of Nitrate on Perchlorate Reduction

The potential inhibitory effect of nitrate on perchlorate reduction was investigated by co-incubating the DM-17 isolate with perchlorate and various levels of nitrate. The initial experiment started with 10 mM sodium perchlorate and either 0, 0.1, 1.0, 10 or 100 mM sodium nitrate, resulting in nitrate to perchlorate ratios of 0x, 0.01x, 0.1x, 1.0x and 10x, respectively. A subsequent experiment started with 1.0 mM of sodium perchlorate and either 0, 0.1, 1.0, 10 or 100 mM sodium nitrate, resulting in nitrate to perchlorate ratios of 0x, 0.1x, 1.0x, 10x, and 100x, respectively. Both experiments were conducted with BMS medium containing 100 mM sodium acetate. Test units consisted of 40 mL borosilicate vials with teflon lined septa. The headspace of each vial was purged with nitrogen gas prior to the start of the experiments. Single measurements of perchlorate, absorbance and pH were measured on each vial at 0, 24, 48 and 72 h. All vials were distributed in an environmental chamber using a fully randomized design. The incubation temperature was maintained at 30° C.

Effect of pH on Perchlorate Reduction

The effect of pH on perchlorate reduction was investigated by incubating the DM-17 isolate in BMS medium containing approximately 5 mM sodium perchlorate and 100 mM sodium acetate at seven different initial pH levels, including 5.5, 6.0, 6.5, 7.0, 7.5, 8.0 and 8.5. Test units consisted of 40 mL borosilicate vials with teflon lined septa. The headspace of each vial was purged with nitrogen gas prior to the start of the experiment. No attempt was made to stabilize the pH using buffers other than that provided by the BMS medium. Measurements of perchlorate, absorbance and pH were taken on three replicate vials at 0, 24 and 48 h. All vials were placed in an environmental chamber and distributed using a fully randomized design. The incubation temperature was maintained at 30° C.

Effect of Temperature on Perchlorate Reduction

The effect of temperature on perchlorate reduction kinetics was investigated by incubating the DM-17 isolate in BMS medium containing approximately 5 mM sodium perchlorate and 100 mM sodium acetate at six different temperatures including 10° C., 15° C., 20° C., 25° C., 30° C. and 35° C. All tempera controlled within water baths to minimize temperature flux. Test units consisted of 40 mL borosilicate vials with teflon lined septa. Each treatment was setup in duplicate. The headspace of each vial was purged with nitrogen gas prior to the start of the experiment. Measurements of perchlorate, chloride, absorbance and pH were taken on three replicate vials at 0, 24, 48 and 72 h.

Perchlorate Reduction Using Various Organic Carbon Sources

Three different plant materials were tested as suitable carbon sources for DM-17. Freshly cut hay, semi-composted straw and senesced cattail (*Typha latifolia*) stalk were each dried at 105° C. for approximately 3 h in a convection oven, then mechanically ground to a coarse powder using a food processor. Approximately 0.6 g (15 g L$^{-1}$) of each material was placed into separate 40 mL borosilicate glass vials. The culture medium consisted of BMS containing 5 mM sodium perchlorate, but no acetate. A mixed culture was prepared by seeding the culture medium with the DM-17 isolate and inoculant collected from the AMPP, described above. Each vial was then topped off with inoculated culture medium. The vials were capped and incubated at 30° C. Perchlorate and pH were measured daily by randomly selecting a replicate vial.

Perchlorate Reduction Using Various Organic Carbon Loadings

Three different loadings (1.0, 5.0 and 15 g L$^{-1}$) of processed cattail were tested to determine the effect of carbon loading on perchlorate reduction kinetics. Senesced cattail stalk was processed as described above. Approximately 0.04 gm (1 g L$^{-1}$), 0.2 gm (5 g L$^{-1}$) or 0.6 gm (15 g L$^{-1}$) of the processed cattail was placed into 40 mL borosilicate glass vials with teflon lined septa. The culture medium consisted of BMS containing 15 mM sodium perchlorate, but no acetate. A mixed culture was prepared by seeding the culture medium with the DM-17 isolate and inoculant collected from the AMPP prepared as described above. Each vial was topped off with inoculated culture medium. Perchlorate, pH and absorbance (600 nm) were measured over a period of 500 h by randomly selecting a replicate vial from each treatment level. Incubation temperature was maintained at 30° C.

Effect of Nitrate on Perchlorate Reduction Using an Organic Carbon Source

This experiment investigated the effects of nitrate on perchlorate reduction by DM-17 when grown in site water containing ground cattail. The experiment used a mixed culture (C2) derived from 5 g L$^{-1}$ fresh and 5 g L$^{-1}$ senesced cattail processed as described above and APS site water collected from the SEW-1 well. Approximately 10 mM sodium perchlorate and 7.5 mM THAM buffer (tris hydroxymethyl aminomethane) were added to the culture. No other amendments were added. Approximately 1 mM of sodium perchlorate was added back to the culture once it was determined that perchlorate was completely eliminated. Four different levels of sodium nitrate were added to 500 mL aliquots of the culture. The treatments consisted of 0, 0.1, 1.0, and 10 mM sodium nitrate, resulting in nitrate to perchlorate ratios of 0x, 0.1x, 1.0x, and 10x, respectively. Test units consisted of 125 mL polyethylene bottles capped with butyl rubber stoppers. The stoppers incorporated 5 mm ports to allow for purging with nitrogen gas after sampling. Four replicates were allocated to each treatment and were sampled hourly for 12 h, then sampled at 24 h. Perchlorate was analyzed on each replicate container, while pH was measured on a single replicate. Incubation temperature was maintained at 29–30° C. Data were analyzed by NCSS 6.0 using repeated measures design and pre-planned orthogonal comparisons as described below.

Perchlorate Reduction Using a Molasses Carbon Source

The use of molasses as an alternate organic carbon source was investigated. A mixed culture (C2) containing the DM-17 isolate was prepared as described in the preceding paragraph. Approximately 1 mM of sodium perchlorate was added back to the culture once determined that the perchlorate was filly reduced. The culture was divided into 500 mL aliquots and raw agricultural grade (48%) molasses was added as the carbon source. The treatments consisted of 0, 0.5, 1.0, and 5 g $L^{-1}$ molasses. Test units were as described. Four replicates were allocated to each treatment and were sampled hourly for eleven hours, then sampled at 23 h. Perchlorate was analyzed on each replicate container, while pH was measured on a single replicate. Incubation temperature was maintained at 29–30° C. Data were analyzed by NCSS 6.0 using repeated measures design and planned orthogonal contrasts between the control (0 g $L^{-1}$ molasses) and each treatment.

Effect of Nitrate on Perchlorate Reduction Using a Molasses Carbon Source

A mixed culture (C2) containing the DM-17 isolate was prepared as previously described. However, no THAM buffer was added. Following complete perchlorate reduction, approximately 1 mM sodium perchlorate and 2 g $L^{-1}$ molasses were added back to the culture. The culture was divided into 500 mL aliquots and four different levels of sodium nitrate were added. The treatments consisted of 0, 0.1, 1.0, 10 and 100 mM sodium nitrate, resulting in nitrate to perchlorate ratios of 0×, 0.1×, 1.0×, 10× and 100×, respectively. Test units consisted of 125 mL polyethylene bottles with 5 mm ports to allow for purging with nitrogen gas after sampling. Four replicates were allocated to each treatment and were sampled hourly for eleven hours, then sampled at 24, 28, 96 and 144 h. Perchlorate was analyzed on each replicate container, while pH was measured on a single replicate. Incubation temperature was maintained at 29–30° C. Data were analyzed by NCSS 6.0 using repeated measures design and planned orthogonal contrasts between the control (0 mM nitrate) and each treatment.

Perchlorate, Chloride, pH, Redox and Absorbance Analysis

Perchlorate ion was measured using an ion specific electrode (model 93-81, Orion Research, Boston, Mass.) and double junction reference electrode (model 90-0281, Orion Research). Ionic strength adjustor (ISA) was prepared as 2 M ammonium sulfate and added at the rate of 2 mL of ISA to 100 mL of sample or standard. A 1:50 dilution of ISA was used as the outer chamber filling solution and saturated silver chloride solution (Orion Cat# 900002) was used as the inner filling solution in the reference electrode. Chloride ion was measured with an ion specific electrode (model 94-17A, Orion Research). All electrodes were used in conjunction with an ion analyzer (model 601A, Orion Research).

The pH was determined using a microcomputer pH meter (Corning Ion Analyzer model 250) and combination pH electrode (Corning model 476530 combination probe). Redox measurements were taken with a platinum combination redox electrode (Corning model 476530). Growth rates of the isolate were based on absorbance readings at 600 nm using a spectrophotometer (Hitachi model U-2000).

Statistical Analysis

For the experiments investigating the perchlorate effect on denitrification, data were analyzed by NCSS 6.0 (v6.0.22, NCSS, Kaysville, Utah). A Randomized Block Analysis of Variance (ANOVA) procedure was used to test the significance of differences between treatments. Duncan's Multiple Comparison test was used to contrast the experimental treatments with the control. The allowable type I error rate (alpha) was set at 5.0%. Perchlorate reduction rates were compared using the F-Test comparison method described by Sokal and Rolhf (1981).

For the experiments investigating isolate performance, data were analyzed by NCSS 2000 (v2000, NCSS, Kaysville, Utah). A Repeated Measures Analysis of Variance (ANOVA) procedure was used to test the significance of differences between treatments and preplanned (a priori) orthogonal comparisons were used to contrast the experimental treatments with the control. The allowable type I error rate (alpha) was set at 5.0%.

Results

Redox and Low Level Perchlorate Reduction Results

Figure 9:
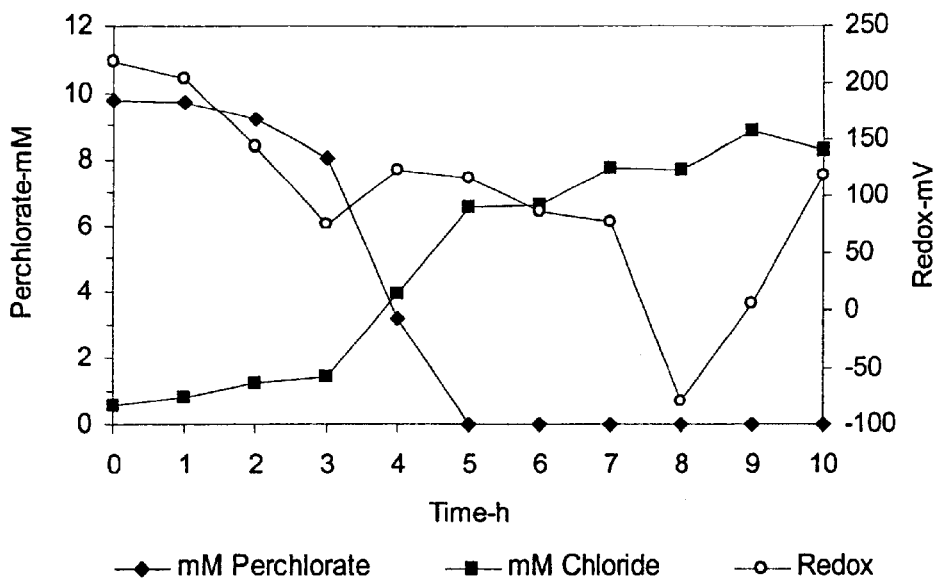
FIG. 9 is a plot of in-situ redox measurement of BMS culture media during perchlorate reduction by the DM-17 bacteria and plots as well perchlorate reduction and resultant chloride all against incubation time.

This experiment was designed to measure the in-situ redox potential of an active DM-1 7 culture growing in BMS medium with perchlorate as the sole electron acceptor. The redox potential was recorded daily with an in-situ redox probe. The initial redox at $t_0$ was +219 mV and declined to a minimum of +76 mV during the first 3 h. FIG. 9 shows in-situ redox measurement of BMS culture medium during active perchlorate reduction by DM-17. Data points are single measurements. The redox remained relatively stable between 3–7 h, then rapidly declined to a minimum of −80 mV at 8 h. It is presumed that oxygen generated by the dismutation of hypochlorite resulted in a stable redox between 3–7 h. Since DM-17 can utilize both perchlorate and oxygen as terminal electron acceptors, the redox remained stable by the simultaneous production and consumption of oxygen. Once the perchlorate was totally consumed, no further oxygen production occurred and the redox declined rapidly. This experiment confirms that DM-17 grows and reduces perchlorate in a microaerophilic environment.

Figure 10:
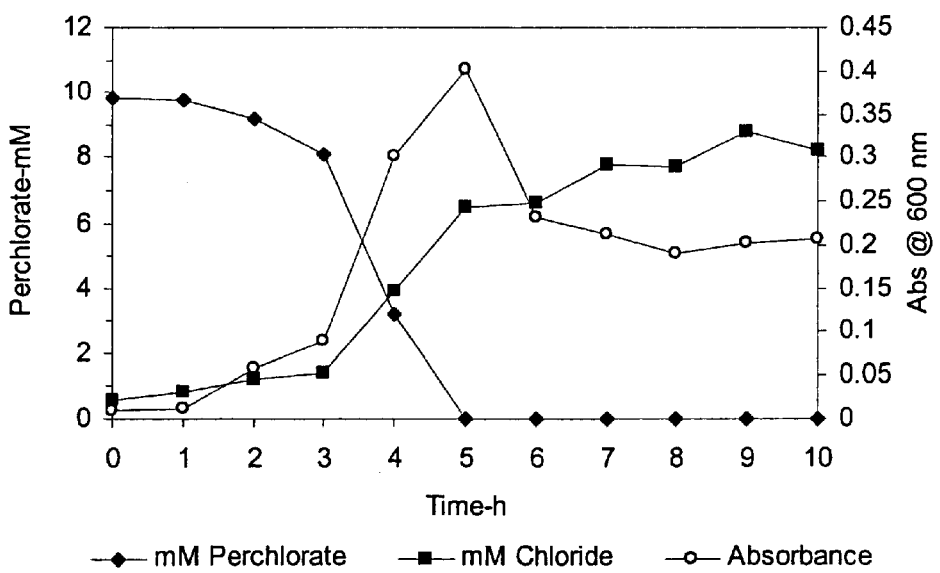
FIG. 10 is a plot of growth rate (absorbance at 600 nm) of the DM-17 bacteria growing in BMS medium and of perchlorate reduction and production of chloride all against incubation time.

It was also determined that the peak density of the culture coincided with the complete reduction of all perchlorate. FIG. 10 illustrates growth rate (absorbance at 600 nm) of DM-17 growing in BMS medium showing simultaneous reduction of perchlorate and production of chloride. Data points are single measurements. The culture rapidly senesced after 5 h indicating that the growth of DM-17 was solely dependent upon the available perchlorate.

Figure 11:
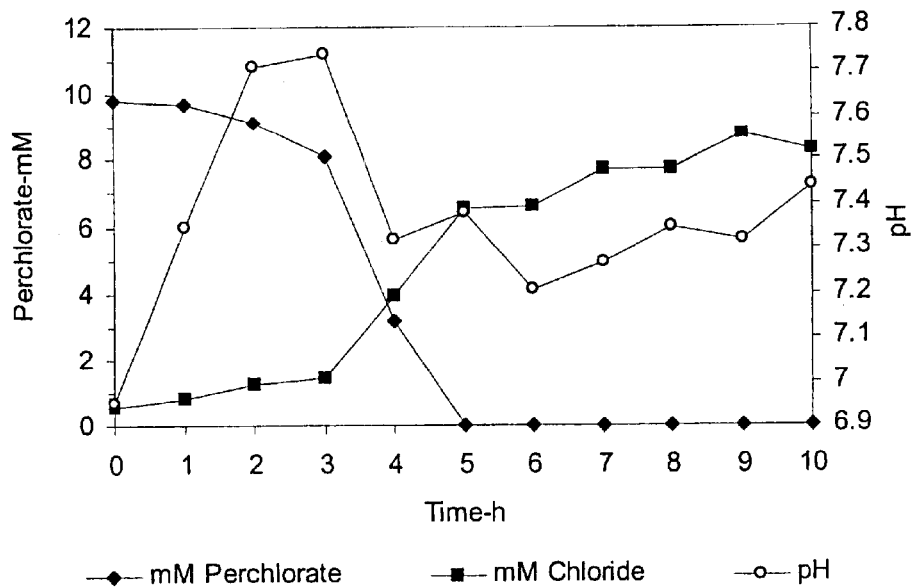
FIG. 11 is a plot of pH of a BMS culture medium against incubation time during perchlorate reduction by the DM-17 bacteria.

The initial pH of the culture was 7.0 and rapidly increased to 7.7 during the first 3 h. FIG. 11 illustrates measured pH of BMS culture medium during active perchlorate reduction by DM-17. Data points are single measurements. The pH subsequently stabilized at 7.3. This finding suggests that the reduction of perchlorate consumes hydrogen ions. In a non-buffered environment, the pH may potentially rise beyond the optimal limits. It is expected that the rise in pH would be offset by heterotrophs releasing volatile organic acids (VOA). The VOA's would tend to offset any increase in pH resulting from the reduction of perchlorate.

Samples were taken from the reactor at 6, 7, 8, 9 and 10 h for low level perchlorate analysis by Montgomery-Watson Laboratories. All samples were less than detectable. Because the laboratory was required to perform a 1:50 dilution of the samples due to interfering anions, the MRL was set at 200 $\mu L^{-1}$. Therefore it can only be determined that the perchlorate was reduced to less than 200 $\mu g$ $L^{-1}$ by the sixth hour.

Chloride ion was also measured throughout the experiment as shown in FIGS. 9, 10 and 11. The rise in chloride ion concentration generally mirrored the decrease in perchlorate. The fastest rise in chloride concentration coincided with the fastest decline in perchlorate concentration, occurring between 3–5 h. Approximately 84% of the expected chloride liberated from perchlorate was accounted for in mass balance. This data demonstrates that the DM-17 isolate is capable of fully reducing perchlorate to chloride.

Inhibitory Effects of Nitrate on Perchlorate Reduction-Results

Figure 12:
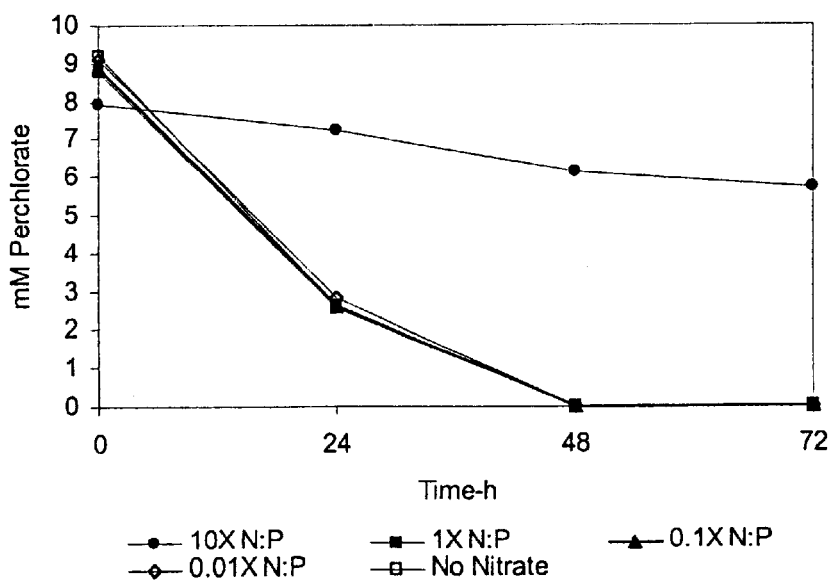
FIG. 12 is a plot of perchlorate versus incubation time during perchlorate reduction by the DM-17 bacteria in BMS medium (at four levels of nitrate) starting with 10 mM sodium perchlorate and having nitrate/perchlorate ratio of 0, 0.01, 0.1 and 10×, respectively.
Figure 13:
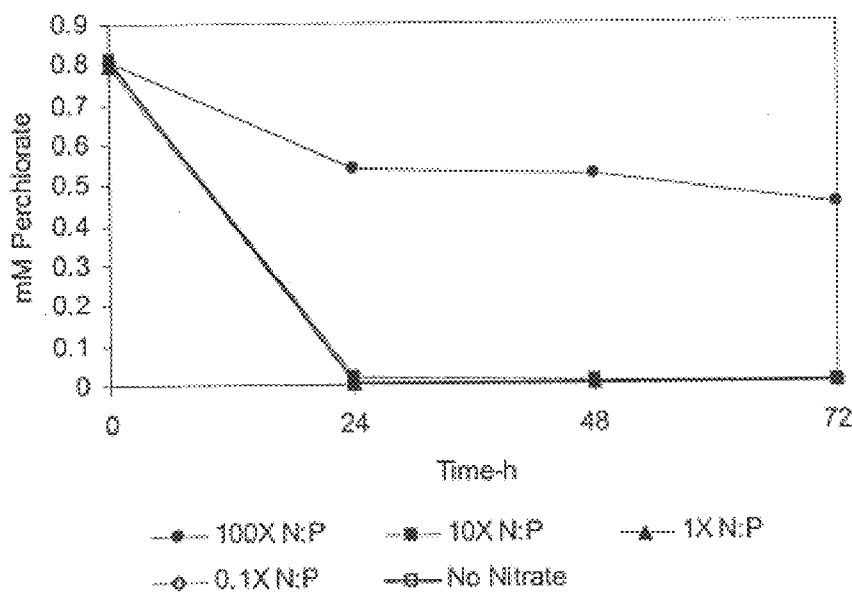
FIG. 13 is a plot like that of FIG. 12 starting with 1 mM sodium perchlorate and having nitrate/perchlorate ratio of 0, 0.1, 1.0, 10 and 10×, respectively.

FIG. 12 illustrates perchlorate reduction by DM-17 grown in BMS medium. The experiment was initiated with 10 mM sodium perchlorate and either 0, 0.1, 1.0, 10 or 100 mM sodium nitrate, resulting in nitrate to perchlorate ratios of 0×, 0.01×, 0.1×, 1.0× and 10×, respectively. Data points represent the mean of triplicate measurements (n=3). FIG. 13 illustrates perchlorate reduction by DM-17 grown in BMS medium. The experiment started with 1 mM sodium perchlorate and either 0, 0.1, 1.0, 10 or 100 mM sodium nitrate, resulting in nitrate to perchlorate ratios of 0×, 0.1×, 1.0×, 10× and 100×, respectively. Data points represent the mean of triplicate measurements (n=3). FIGS. 12 and 13 show that perchlorate reduction by DM-17 was inhibited by high nitrate concentrations. FIG. 12 shows that only the treatment with 100 mM nitrate (10×) was inhibitory, since the 0×, 0.01×, 0.1×, and 1× treatments all removed greater than 99.9% of the initial perchlorate within 48 h. The 10× (10 mM) treatment only reduced 22.5% of the initial perchlorate by 48 h. Likewise, FIG. 13 shows that only the 100 mM nitrate (100×) was inhibitory, since the 0×, 0.1×, 1.0×, and 10× treatments all removed greater than 99% of the initial perchlorate by 48 h. The 100× treatment only reduced 35.1% of the initial perchlorate within 48 h.

Effect of pH On Perchlorate Reduction-Results

Figure 14:
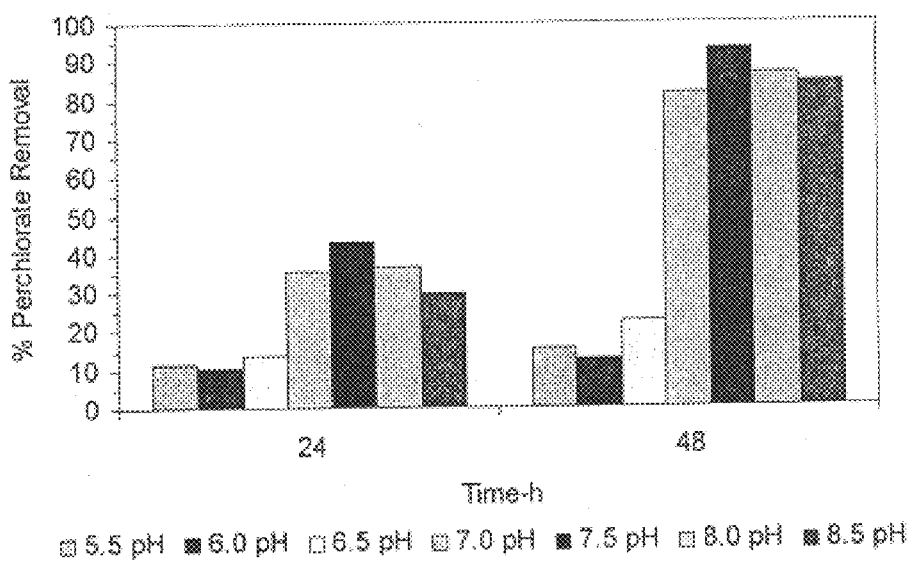
FIG. 14 is a series of bar graphs showing, at 24 and 48 hours of incubation, perchlorate removal by the DM-17 bacteria grown in BMS medium at various pH levels.

This experiment focused on pH optima and pH tolerance of the DM-17 isolate. FIG. 14 illustrates perchlorate reduction (% removal) by DM-17 grown in BMS medium at various pH levels. Initial pH treatments included 5.5, 6.0, 6.5, 7.0, 7.5, 8.0 and 8.5. The buffering capability of the growth medium was limited, therefore the pH levels were free to fluctuate based upon the biochemical response of the culture. Data points represent the mean of triplicate measurements (n=3). The pH 7.5 treatment performed best overall, indicated by 92.7% reduction within 48 h. However, the pH 7.0, 8.0 and pH 8.5 treatments all demonstrated similar rates and reduced the perchlorate by 81.0%, 86.4%, and 84.3%, respectively. The pH 5.5, 6.0, and 6.5 treatments showed significantly slower rates and reduced the perchlorate within 48 h by 15.3%, 12.3%, and 22.6%, respectively.

The final pH at 48 h of the 7.5, 8.0 and 8.5 treatments all decreased to 7.2, 7.3 and 7.3, respectively, explaining the similar rates after 24 h. The final pH at 48 h of the 5.5, 6.0, 6.5 and 7.0 treatments were 5.5, 6.1, 6.9 and 7.0, respectively. Thus, the treatments having an initial pH of 7.0 or less did not demonstrate a change in pH.

Effect of Temperature on Perchlorate Reduction-Results

Figure 15:
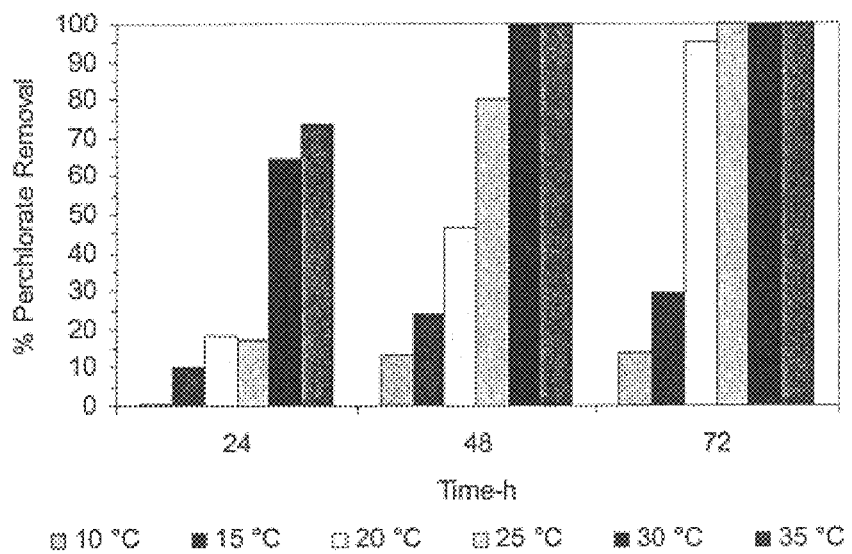
FIG. 15 is a series of bar graphs showing, at 24, 48, and 72 hours of incubation, perchlorate removal by the DM-17 bacteria grown in the BMS medium at various temperatures.

This experiment investigated the effect of temperature on the kinetics of perchlorate reduction by a mature culture of DM- 17. FIG. 15 illustrates perchlorate reduction (% removal) by DM-17 grown in BMS medium at various temperatures. Temperatures during experiment were constant at 10, 15, 20, 25, 30 and 35° C., however, the culture was initially grown at 30° C. Data points represent the mean of triplicate measurements (n=3). The effect of temperature on the growth of DM-17 was not explored in this experiment since each treatment began with mature cultures initially grown at 30° C.

The optimal temperature was determined to be at least 35° C. At 35° C., 73.5% of the initial perchlorate was reduced within 24 h. By 24 h, the 10, 15, 20, and 30° C. treatments yielded 0.56%, 10.4%, 18.1%, and 64.5% reduction, respectively. Within 48 h, the 10, 15, 20, 25, 30 and 35° C. treatments yielded 13.6%, 24.1%, 46.6%, 80.1%, 99.9% and 99.8% reduction, respectively. The result for the 25° C. treatment at 24 h was considered erroneous due to incubator failure.

Perchlorate Reduction Using Various Organic Carbon Sources-Results

Figure 16:
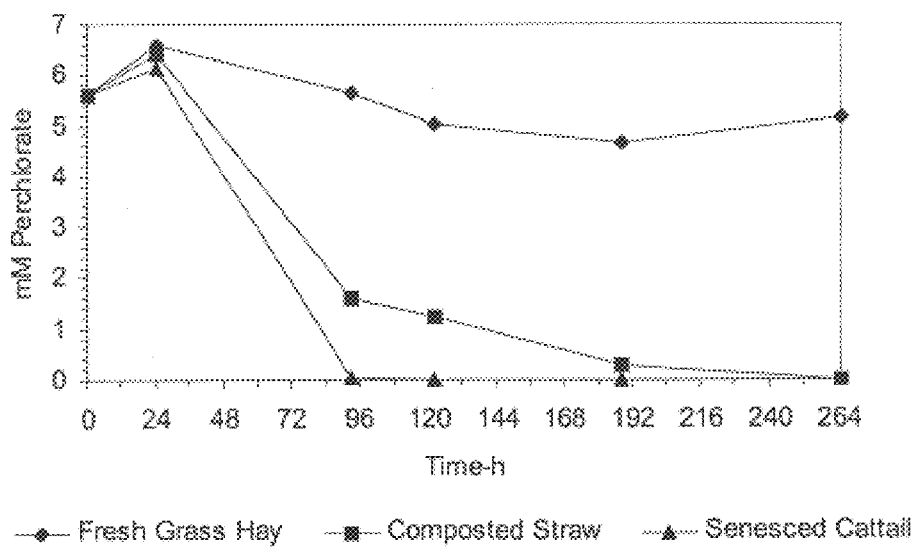
FIG. 16 is a plot of perchlorate versus incubation time during perchlorate reduction by the DM-17 bacteria grown at 30° C. in mixed culture with three different organic carbon sources.

This experiment investigated the potential of three different plant materials to serve as sole carbon sources. FIG. 16 illustrates perchlorate reduction by isolate DM-17 grown at 30° C. in mixed culture containing three different organic carbon sources. Treatments included fresh cut grass hay, composted straw and senesced cattail stalk. All plant materials were dried at 105° C. and coarsely ground. Data points are single measurements. Treatments included fresh cut grass hay (FGH), composted straw (CS), and senesced cattail stalk (SCT). FIG. 16 shows that the SCT material performed the best overall, with over 99% removal within 93 h and 99.9% removal within 188 h. The CS material performed moderately well with 71.1% removal within 93 h and 94.6% removal within 188 h. Finally, the FCH material performed poorly with no removal at 93 h and 16.8% removal at 188 h. The pH of the FGH culture was less than 6.0 throughout the experiment, perhaps explaining the poor performance of the culture. Previous studies (see "Effect of pH on Perchlorate Reductions-Results" above) concluded that perchlorate reduction was severely inhibited when pH of the culture fell below 6.5.

Perchlorate Reduction Using Various Organic Carbon Loadings-Results

Figure 17:
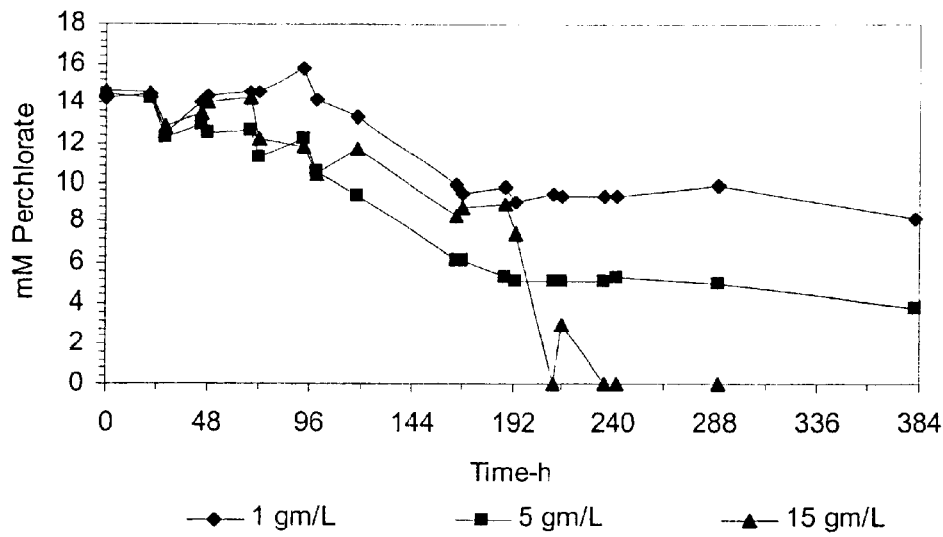
FIG. 17 is a plot of perchlorate versus incubation time during perchlorate reduction by the DM-17 bacteria grown at 30° C. in mixed culture containing three different content levels of dried cattail.

Since cattail (SCT) material proved to be the best organic carbon source of the three types tested, this experiment investigated optimal loading rates of SCT. FIG. 17 illustrates perchlorate reduction by isolate DM-17 grown at 30° C. in mixed culture containing dried cattail as the sole organic carbon source. Treatments included 1.0, 5.0 or 15 g $L^{-1}$ processed cattail. Data points are single measurements. Experimental treatments included 1.0, 5.0 and 15 g $L^{-1}$ processed cattail prepared in SEW-1 sitewater. Perchlorate reduction by isolate DM-17 grown at 30° C. in mixed culture was measured over 382 h in each of the three treatments.

FIG. 17 shows that the 15 g $L^{-1}$ treatment performed the best, but all treatments showed similar kinetics rates during the first 194 h. The 15 g $L^{-1}$ treatment rapidly reduced perchlorate between 194 and 212 h. Although the 1.0 and 5.0 g $L^{-1}$ treatments provided a sufficient carbon source for the culture, the redox was more favorable to perchlorate reduction within the 15 g $L^{-1}$ treatment due to the added biochemical oxygen demand (BOD).

Figure 18:
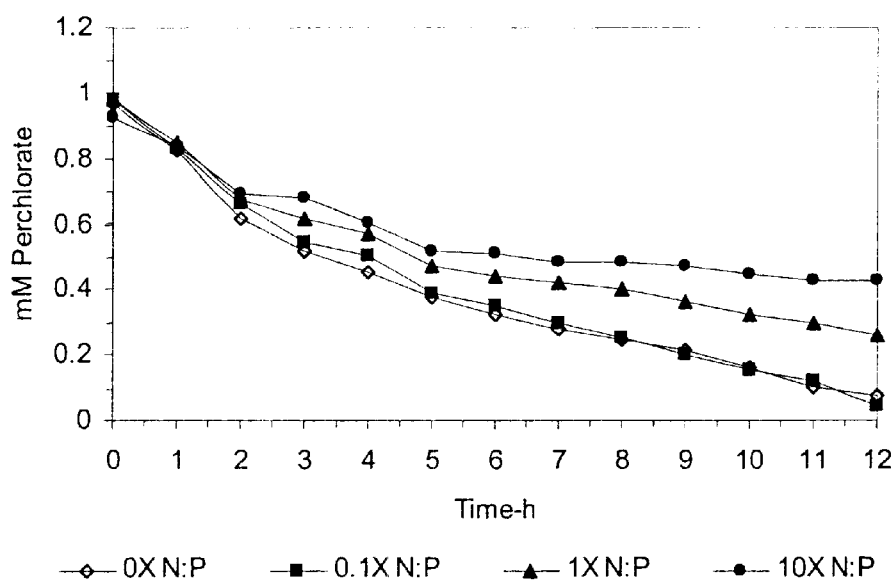
FIG. 18 is a plot of perchlorate versus incubation time during perchlorate reduction by the DM-17 bacteria grown at 30° C. in mixed culture containing site water, senesced and dried fresh cattail and various levels of sodium nitrate.

Effect of Nitrate On Perchlorate Reduction Using an Organic Carbon Source-Results This experiment was designed to investigate the inhibitory effects of nitrate when cattail (10 g $L^{-1}$ dried fresh cattail and 10 g $L^{-1}$ dried senesced cattail) was the sole carbon source. Three levels of nitrate (0.1, 1.0 and 10 mM sodium nitrate) were compared to a control without added nitrate. FIG. 18 illustrates perchlorate reduction by isolate DM-17 grown at 30° C. in mixed culture containing SEW-1 site water (nitrate consumed), 10 g $L^{-1}$ dried senesced cattail, 10 g $L^{-1}$ dried fresh cattail and either 0, 0.1, 1.0, or 10 mM sodium nitrate (0×, 0.1×, 1.0×, and 10× nitrate:perchlorate). Data points are based on the mean of four replicates (n=4). FIG. 18 shows that kinetic rates were diminished when DM-17 was grown in 1 mM and 10 mM sodium nitrate. Within 12 h of incubation, the 0×, 0.1×, 1× and 10× treatments reduced perchlorate levels by 91.7%, 95.2%, 73.5% and 53.5%, respectively. By 24 h, the 0×, 0.1×, 1× and 10× treatments reduced perchlorate levels by 99.2%, 99.2%, 98.4% and 76.0%, respectively.

The kinetic curves of the control and 0.1× (0.1 mM nitrate) treatment were nearly identical throughout the course of the experiment. Pre-planned orthogonal comparisons (repeated measures design) between the control and 0.1× treatment did not show significant differences (p=0.22), however, comparisons between the control and the 1× and 10× treatments did show significant differences (p<0.000001).

Figure 19:
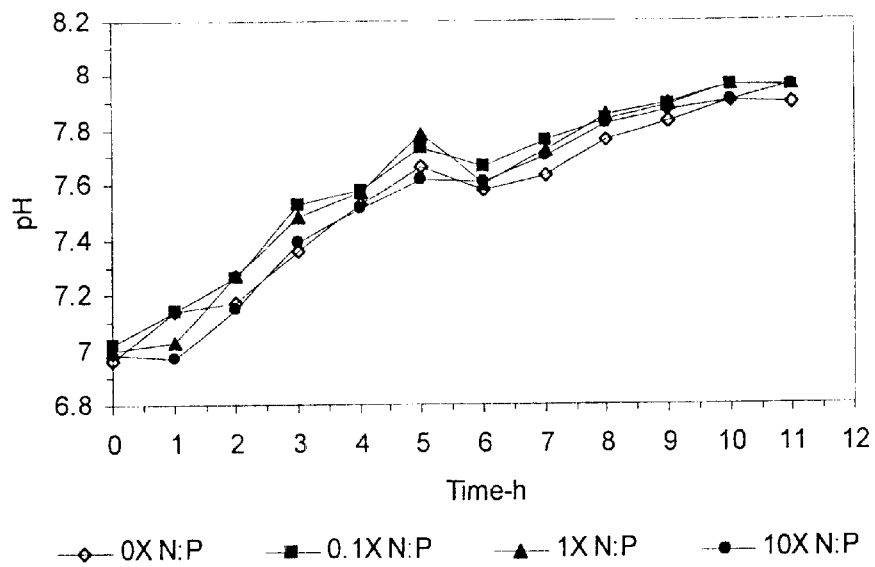
FIG. 19 is a plot of pH versus incubation time of culture medium containing the DM-17 bacteria grown at 30° C. in mixed culture containing site water, senesced and dried fresh cattail and various levels of sodium nitrate.

FIG. 19 illustrates the pH of culture medium containing DM-17 grown at 30° C. in mixed culture prepared with SEW-1 site water (nitrate consumed), 10 g $L^{-1}$ dried senesced cattail, 10 g $L^{-1}$ dried fresh cattail and either 0, 0.1, 1.0, or 10 mM sodium nitrate (0×, 0.1×, 1.0×, and 10× nitrate:perchlorate). Data points are single measurements. The pH of the culture medium increased throughout the experiment as shown in FIG. 19. The average initial pH of all treatments was 7.0 and peaked at 7.9. Since all treatments showed similar pH patterns, it is likely that the pH change was independent of nitrate concentration. It should be noted that this experiment used a THAM buffer which would be expected to buffer or stabilize the pH.

Perchlorate Reduction Using a Molasses Carbon Source-Results

Figure 20:
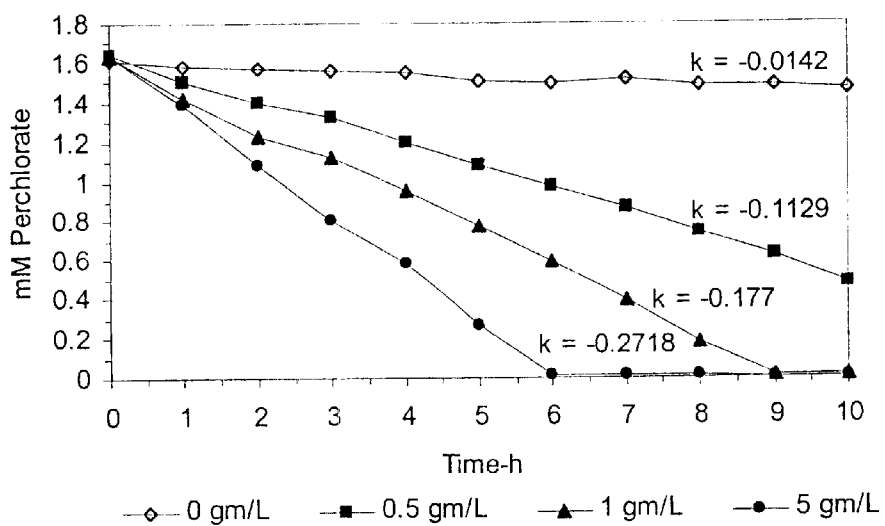
FIG. 20 is a plot of perchlorate versus incubation time during perchlorate reduction by the DM-17 bacteria grown at 30° C. in mixed culture containing dried cattail and different levels of molasses.

This experiment investigated the potential of molasses to accelerate the kinetics of perchlorate reduction. Samples from four replicates of each treatment (0, 0.5, 1.0 and 5.0 g $L^{-1}$) were taken hourly for the first 10 h and at 23 h. FIG. 20 illustrates perchlorate reduction by isolate DM-17 grown at 30° C. in mixed culture prepared with SEW-1 site water (nitrate consumed), 10 g $L^{-1}$ dried cattail and 0, 0.5, 1.0 or 5 g $L^{-1}$ molasses (48%). All data points are based on mean of four replicates (n=4). FIG. 20 shows the zero order kinetic curves for 0, 0.5, 1 and 5 g $L^{-1}$ of 48% molasses. All treatments containing molasses performed significantly better than the control without added molasses (repeated measures design-planned orthogonal comparisons, p<0.000001. Zero order rate constants (mM $h^{-1}$) determined for the 0, 0.5, 1 and 5 g $L^{-1}$ treatments were −0.0142, −0.1129, −0.177, and −0.2718, respectively. The rate constants were strongly correlated with molasses loading. The 0, 0.5, 1 and 5 g $L^{-1}$ molasses treatment required 112, 14.5, 9.2 and 6 h residence time, respectively, for reduction to non-detectable levels (<10 µM perchlorate).

Figure 21:
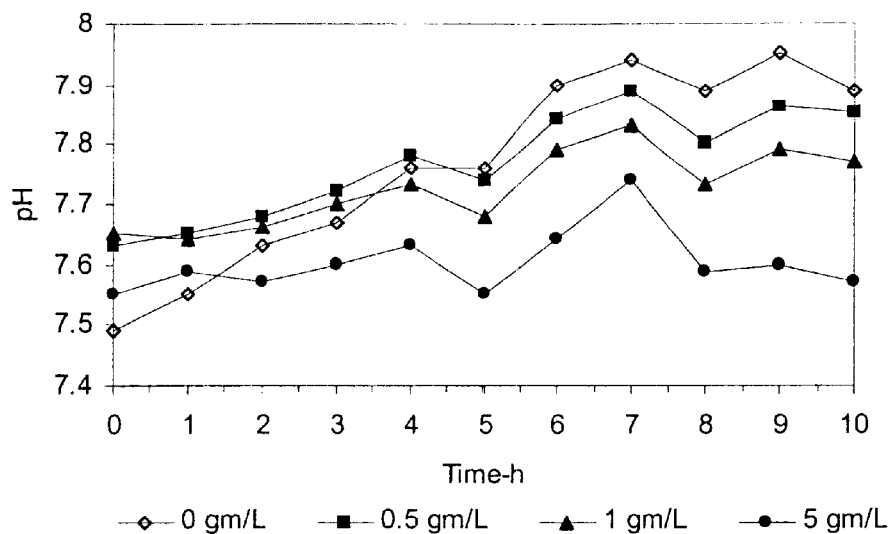
FIG. 21 is a plot of pH versus incubation time of culture medium with DM-17 grown at 30° C. in mixed culture containing dried cattail and different levels of molasses.

FIG. 21 illustrates the pH of culture medium with DM-17 grown at 30° C. in mixed culture prepared with SEW-1 site water (nitrate consumed), 10 g $L^{-1}$ dried cattail and 0, 0.5, 1.0 or 5 g $L^{-1}$ molasses (48%). Data points are single measurements.

Effect of Nitrate on Perchlorate Reduction Using a Molasses Carbon Source-Results Since molasses was very effective at accelerating perchlorate reduction, this experiment investigated the role of nitrate as an inhibitor in the presence of molasses and cattail. Samples from four replicates of each treatment containing 1.0 mM perchlorate and either 0, 0.1, 1.0, 10 or 100 mM sodium nitrate (representing 0×, 0.1×, 1.0×, 10× and 100× nitrate:perchlorate) were taken hourly at 0–11 h and at 24 h.

Figure 22:
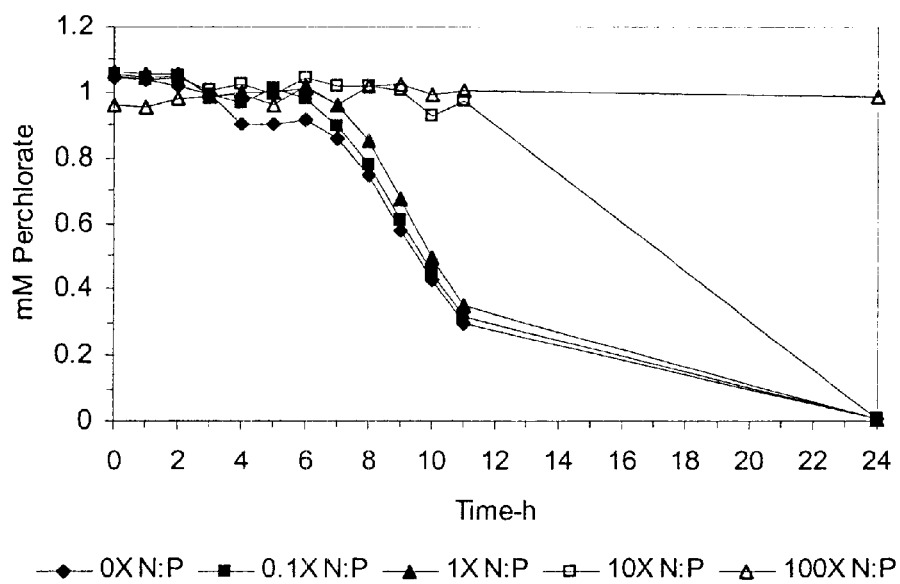
FIG. 22 is a plot of perchlorate versus incubation time during perchlorate reduction by the DM-17 bacteria grown at 30° C. in mixed culture with dried cattail, molasses and different levels of nitrate.

FIG. 22 illustrates perchlorate reduction by isolate DM-17 grown at 30° C. in mixed culture prepared with SEW-1 site water 10 g $L^{-1}$ dried cattail, 2 g $L^{-1}$ molasses (48%) and either 0, 0.1, 1.0, 10 or 100 mM sodium nitrate (0×, 0.1×, 1.0×, 10× and 100× nitrate: perchlorate). Data points are based on the mean of four replicates (n=4). FIG. 21 shows the kinetic curves for each treatment. All treatments containing nitrate were significantly different compared to the control without added nitrate (repeated measures design-planned orthogonal comparisons, p<0.000001. Zero order rate constants (mM $h^{-1}$) for the 0×, 0.1×, 1.0×, and 10× treatments were −0.130, −0.138, − 0.140, and −0.0.018, respectively. The 0.1× and 1× treatments actually yielded greater rate constants compared to the 0× treatment and is consistent with the data discussed in Isolate Characterization above.

Based on assumed zero order kinetics and 1.0 mM (100 mg/L) initial perchlorate concentration, a zero order kinetic model suggests the 0×, 0.1×, 1.0×, and 10× treatments would require 7.7, 7.3, 7.1 and 55.9 h residence time for elimination to non-detectable levels (<10 µM perchlorate), respectively. The 100× treatment showed no appreciable perchlorate reduction within 44 h.

Although specific, preferred embodiments of the invention have been described in detail herein, it will be apparent to one skilled in the art that modifications can be made without departure from the spirit and scope of the invention as set forth in the appended claims.

BIBLIOGRAPHY

1. Anbar, M., S. Guttmann and Z. Lewitus. 1959. The mode of action of perchlorate ions on the iodine uptake of the thyroid gland. Int. J. Appl. Radiat. Isot. 7:87–96.
2. Attaway, H. and M. Smith. 1993. Reduction of perchlorate by an anaerobic enrichment culture. J. Industrial Microbiology 12:408–412.
3. Bergy's Manual. 1984. Bergy's Manual of Systematic Bacteriology. Edited by N. R. Krieg. Williams and Wilkins, Baltimore, Md.
4. Coates, J. D., U. Michaelidou, R. A. Bruce, S. M. O'C.onnor, J. N. Crespi and L. A. Achenbach. 1999. Ubiquity and diversity of dissimilatory (per)chlorate-reducing bacteria. Appl. Environ. Microbiol. 65(12): 5234–5241.
5. Dendooven, L. and J. M. Anderson. 1994. Dynamics of reduction enzymes involved in the denitrification process in pasture soil. Soil Biol. Biochem. 26 (11):1501–1506.
6. Dendooven, L. and J. M. Anderson. 1995. Use of a ìleast squareî optimization procedure to estimate enzyme characteristics and substrate affinities in the denitrification reactions in soil. Soil Biol. Biochem. 27 (10):1261–1270.
7. Focht, D. D. 1994. Microbiological procedures for biodegradation research. p 407–426. In *Methods of Soil Analysis*, Part 2. SSSA Book Ser. 5. SSSA, Madison, Wis.
8. Frankenberger, N. T. Jr. and D. C. Herman. 2000. Bacterial Removal of Perchlorate and Nitrate. U.S. Pat. No. 6,077,429.
9. Giblin, T. L., D. C. Herman and W. T. Frankenberger, Jr. 1999. An autotrophic system for the bioremediation of perchlorate from groundwater, p.199–211. in *Perchlorate in the Environment* (E. T. Urbansky, ed). Kluwer Academic/Plenum Publishers, New York, N.Y.
10. Giblin T., D. Herman, M. A. Deshusses and W. T. Frankenberger, Jr. 2000. Removal of perchlorate in ground water with a flow-through bioreactor. J. Environ. Qual. 29:578–583.
11. Herman, D. C. and W. T. Frankenberger Jr. 1999. Bioremediation and biodegradation, bacterial reduction of perchlorate and nitrate in water. J. Environ. Qual. 28:1018–1024.
12. Logan, B. E., K. Kim, J. Miller, P. Mulvaney, J. Wu, H. Zhang and R. Unz. 1999. Factors affecting biodegradation of perchlorate contaminated waters. In *Proceedings of the Perchlorate in the Environment Symposium*, Aug. 22–26, 13. Malmqvist, A., T. Welander, and L. Gunnarsson. 1991. Anaerobic growth of microorganisms with chlorate as an electron acceptor. Appl. Environ. Microbiol. 57(8):2229–2232.
14. Malmqvist, A., T. Welander, E. Moore, A. Ternstrom, G. Molin, ad I. M. Stenstrom. 1994. Ideonella dechloratans gen. nov., sp. nov., a new bacterium capable of growing anaerobically with chlorate as an electron acceptor. System. Appl. Microbiol. 17:58–64.
15. Michaelidou, U., L. A. Achenbach and J. D. Coates. 1999. Isolation and characterization of two novel (per)chlorate-reducing bacteria from swine waste lagoons In *Proceedings of the Perchlorate in the Environment Symposium,* Aug. 22–26, 1999 (E. T. Urbansky and M. R. Schock, eds). Division of Environmental Chemistry, American Chemical Society, New Orleans, La.
16. Miller, J. P. and B. E. Logan. 2000. Sustained perchlorate degradation in an autotrophic, gas-phase, packed-bed bioreactor. Environ. Sci. Technol. 34:3018–3022.
17. Nzengung, V. A. and C. Wang. 1999. Influences on phytoremediation of perchlorate contaminated water. In *Proceedings of the Perchlorate in the Environment Symposium,* Aug. 22–26, 1999 (E. T. Urbansky and M. R. Schock, eds). Division of Environmental Chemistry, American Chemical Society, New Orleans, La.
18. Rikken, G. B., A. G. M. Kroon and C. G. van Ginkel. 1996. Transformation of (per)chlorate into chloride by a newly isolated bacterium; reduction and dismutation. Appl. Microbiol. Biotechnol. 45:420–426.
19. Sokal R. R. and F. J. Rohlf. 1981. Biometry: The Principles and practice of statistics in biological research. W. H. Freeman, San Francisco, Calif.
20. Stanbury, J. B. and J. B. Wyngaarden. 1952. Effect of perchlorate on the human thyroid gland. Metabolism 1:533–539.
21. Wallace, W. T., T. Ward, A. Breen, and H. Attaway. 1996. Identification of an anaerobic bacterium which reduces perchlorate and chlorate as Wolinella succinogenes. J. Ind. Microbiol. 16:68–72.
22. Wolff, J. 1998. Perchlorate and the thyroid gland. Pharmacol. Rev. 50:89–105.

We claim:

1. A method for removing nitrate and/or perchlorate from a material which is contaminated with nitrate and/or perchlorate, comprising:
   (a) providing bacteria DM-17; and
   (b) contacting the material with the DM-17 bacteria under conditions whereby said bacteria are capable of reducing said nitrate and/or perchlorate.

2. The method according to claim 1, for removing nitrate from a material contaminated with nitrate, wherein the material contacted with the DM-17 bacteria in the presence of perchlorate.

3. The method according to claim 2, wherein contacting the material in the presence of perchlorate further comprises pretreating the bacteria with perchlorate prior to contacting the material.

4. The method according to claim 1, further comprising maintaining the DM-17 bacteria in contact with the material which is contaminated with nitrate for a period of time at an at least partially reduced level of oxygen content.

5. The method according to claim 4, wherein the material is maintained in contact with the bacteria for the period of time anaerobically.

6. The method according to claim 4, wherein the bacteria are maintained in contact with the material for the period of time under microaerophylic conditions.

7. The method according to claim 1, wherein contacting the material with the bacteria in the presence of perchlorate comprises contacting the material in the presence of less than 1.0 mM perchlorate.

8. The method according to claim 7, wherein contacting the material with the bacteria DM-17 in the presence of perchlorate comprises contacting the material in the presence of substantially 0.1 mM perchlorate.

9. The method of claim 1, comprising in addition providing a carbon source in contact with the material and the bacteria.

10. The method according to claim 9, wherein the carbon source comprises at least one of acetate, an organic plant and a sugar source.

11. In a method for removing perchlorate from a material which is contaminated with perchlorate, said method comprising treating said material with a bacteria to remove said perchlorate; the improvement comprising using a bacteria DM-17, as the bacteria in said treatment.

12. The method for removing perchlorate according to claim 11, further comprising treating said material with the bacteria in presence of nitrate.

13. The method according to claim 12, wherein treating the material with the bacteria in the presence of nitrate further comprises treating the material in the presence of less than 1.0 mM of the nitrate.

14. The method according to claim 13, wherein treating the material in the presence of nitrate comprises treating the material in the presence of substantially 0.1 mM of the nitrate.

15. The method for removing perchlorate according to claim 12, wherein treating the material further comprises treating the material with the bacteria to remove the nitrate.

16. The method for removing perchlorate according to claim 12, wherein treating the material with a bacteria in the presence of nitrate to remove the perchlorate comprises mixing the bacteria with the material and maintaining the mixture at an incubation temperature at or above 25° C.

17. The method for removing perchlorate according to claim 16, wherein the incubation temperature is at or above 35° C.

18. The method according to claim 12, wherein treating the material with the bacteria in the presence of nitrate to remove the perchlorate comprises mixing the bacteria with the material and maintaining the mixture at a pH of 6.5 or higher.

19. The method according to claim 18, wherein the pH is at least substantially 7.5.

20. The method according to any one of claims 11–19, wherein treating the material with the bacteria includes treating the material with the bacteria in the presence of a carbon source.

21. The method according to claim 20, wherein the carbon source comprises one or more organic plant substance.

22. The method according to claim 20, wherein the carbon source comprises at least one of acetate, hay, straw, cattail, and molasses.

23. The method according to claim 22, wherein carbon source comprises dried fresh cattail.

24. The method according to claim 22, wherein the carbon source comprises senesced cattail.

25. The method according to claim 22, wherein the carbon source comprises dried fresh cattail and molasses.

26. The method according to claim 22, wherein the carbon source comprises senesced cattail and molasses.

27. The method according to any one of claims 11–19; further comprising bringing the amount of nitrate into a range from 0.1:1 to 10:1 nitrate: perchlorate.

28. The method according to claim 27, wherein the nitrate is brought into the range greater than 0:1 and less than 1:1 nitrate: perchlorate.

29. The method according to any one of claims 11–19, further comprising bringing the amount of nitrate into an amount not more than 10 mM.

30. The method according to claim 11, further comprising treating said material with the bacteria in the presence of at least one of marsh sediment and trace heavy metals.

31. The method according to claim 11, wherein the step of treating the material comprises treating the material under an aerobic or microaerophylic condition.

32. A composition for use in treating contaminated material under anaerobic or microaerophylic conditions to remove perchlorate and/or nitrate therefrom, said composition comprising a bacteria DM- 17, a growth medium for said DM-17 bacteria, and a carbon source.

33. The composition according to claim 32, wherein the carbon source comprises an organic plant substance.

34. The composition according to claim 32, wherein the carbon source comprises at least one of acetate, hay, straw, cattail and molasses.

35. The composition according to claim 32, wherein the carbon source is a sugar source.

36. The composition according to claim 32, further comprising a nitrate, and wherein the composition is for use in removal of perchlorate.

37. The composition according to claim 36, wherein the nitrate comprises less than 1.0 mM nitrate.

38. A biologically pure culture of a bacteria DM-17.

39. A method for removing perchlorate and nitrate from a material that is contaminated with perchlorate and nitrate, the method comprising contacting the material with a bacteria DM-17 to remove the perchlorate and the nitrate.

40. The method according to claim 39, wherein contacting comprises contacting the material in the presence of a carbon source.

41. A method for removing nitrate from a material contaminated with nitrate comprising contacting the material with DM-17 bacteria, and adding at least one of perchlorate, organic plant material carbon source, and molasses.

42. A method for removing perchlorate from a material which is contaminated with perchlorate comprising contacting the material with the DM-17 bacteria and adding at least one of nitrate, organic plant material carbon source, and molasses.

43. The method according to either claim 41 or claim 42, wherein the step of adding includes adding the organic plant material carbon source selected from the group consisting of acetate, hay, straw and cattail.

44. A method for removing perchlorate and/or nitrate from a material which is contaminated with perchlorate and/or nitrate comprising contacting the material with DM-17 bacteria and adding organic plant material carbon source, or molasses.

* * * * *